(12) United States Patent
Fenkart et al.

(10) Patent No.: US 6,430,255 B2
(45) Date of Patent: Aug. 6, 2002

(54) NONINTRUSIVE INSPECTION SYSTEM

(75) Inventors: Gerhard Fenkart, Zurich (CH); François A. Mesqui, Palo Alto, CA (US); David E. Kresse, Walnut Creek, CA (US); William H. Baylis, Tiburon, CA (US)

(73) Assignee: InVision Technologies, Inc., Newark, CA (US)

( * ) Notice: Subject to any disclaimer, the term of this patent is extended or adjusted under 35 U.S.C. 154(b) by 0 days.

(21) Appl. No.: 09/794,505

(22) Filed: Feb. 26, 2001

Related U.S. Application Data

(63) Continuation of application No. PCT/US99/28229, filed on Nov. 29, 1999.
(60) Provisional application No. 60/110,417, filed on Nov. 30, 1998.

(51) Int. Cl.$^7$ ............................................... G01N 23/04
(52) U.S. Cl. ................................. 378/57; 378/203
(58) Field of Search ............................ 378/51, 57, 203, 378/208

(56) References Cited

U.S. PATENT DOCUMENTS

| | | | |
|---|---|---|---|
| 4,020,346 A | * 4/1977 | Dennis | 250/519.1 |
| 4,239,969 A | 12/1980 | Haas et al. | 250/359 |
| 4,465,540 A | 8/1984 | Albert | 156/252 |
| 4,495,636 A | 1/1985 | Jacobs et al. | 378/87 |
| 4,879,735 A | * 11/1989 | Owens | 250/359.1 |
| 5,124,554 A | 6/1992 | Fowler et al. | 350/358.1 |
| 5,182,764 A | 1/1993 | Peschmann et al. | 378/57 |
| 5,367,552 A | 11/1994 | Peschmann | |
| 5,479,021 A | 12/1995 | Morgan et al. | 250/363.04 |
| 5,754,617 A | * 5/1998 | Itoh | 378/4 |
| 5,901,198 A | 5/1999 | Crawford et al. | 378/57 |
| 5,982,843 A | 11/1999 | Bailey et al. | |

FOREIGN PATENT DOCUMENTS

| | | |
|---|---|---|
| WO | WO 98/58389 | 12/1998 |
| WO | PCT/US 99/28229 | 11/1999 |

* cited by examiner

*Primary Examiner*—David P. Porta
(74) *Attorney, Agent, or Firm*—Blakely, Sokoloff, Taylor & Zafman

(57) ABSTRACT

An x-ray technique-based nonintrusive inspection apparatus is provided which is capable of inspecting 600 containers an hour which is small, and which is easily maintainable. Features of the apparatus include "radiation locking" with "active curtains", "continuous scanning" utilizing an x-ray line scanner subsystem and a CT scanner subsystem, good structural integrity, radiation containment in a self-shielding manner, an easily maintainable driving arrangement, shielding curtains that can be raised and lowered quickly, a container jam release mechanism, and efficient air conditioning.

16 Claims, 14 Drawing Sheets

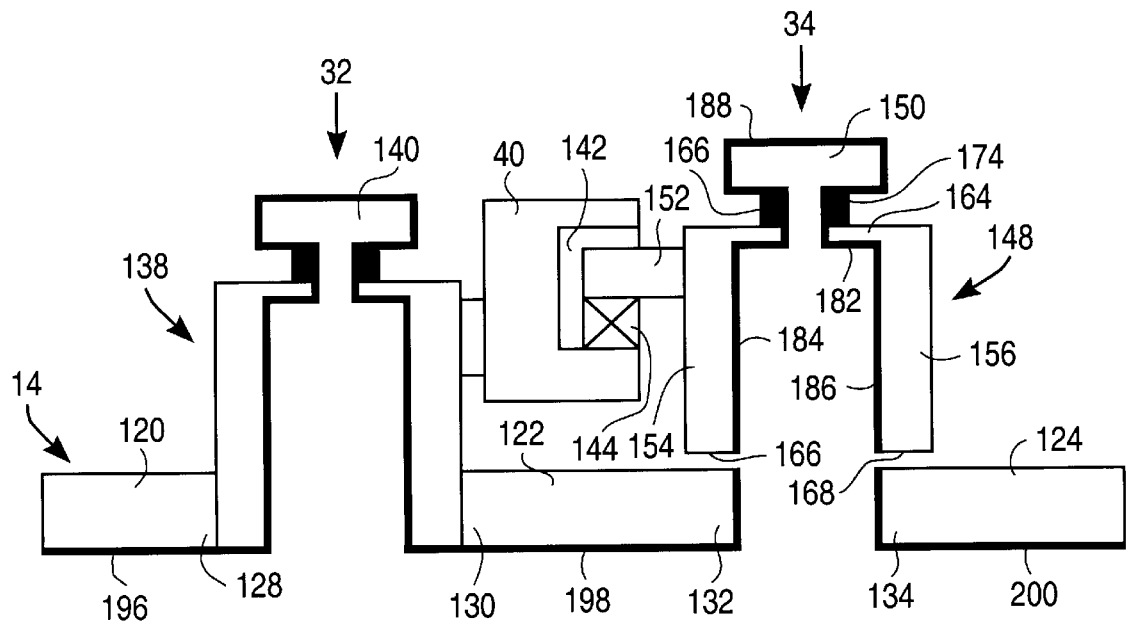
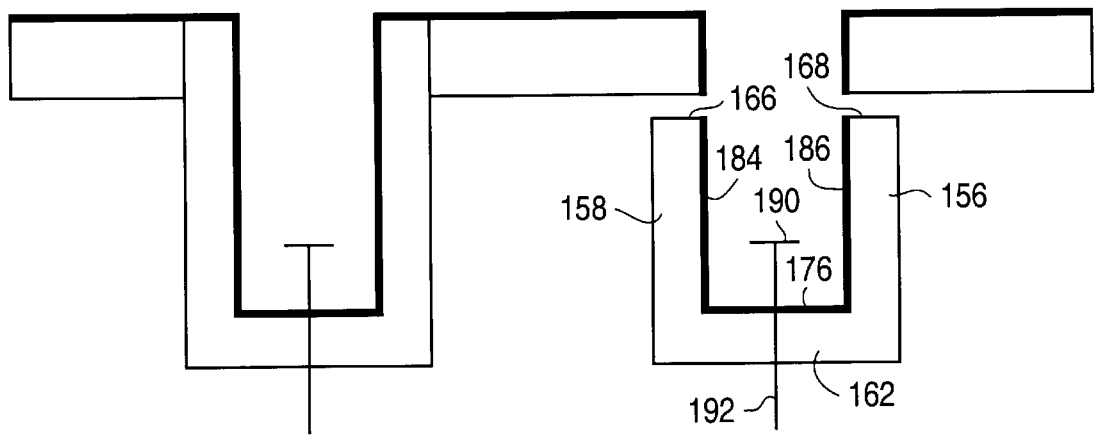
FIG. 6

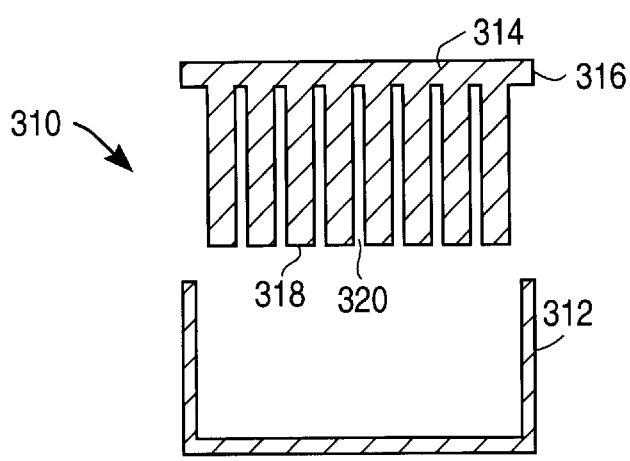 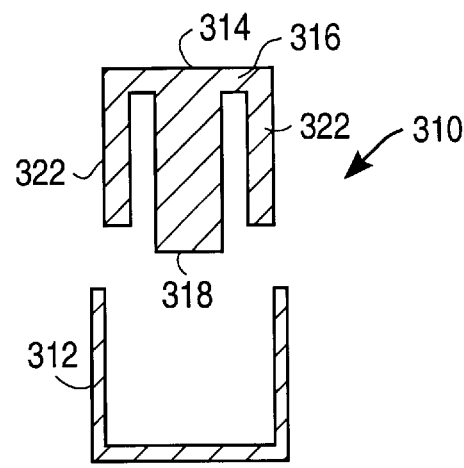
FIG. 12a(i)    FIG. 12a(ii)
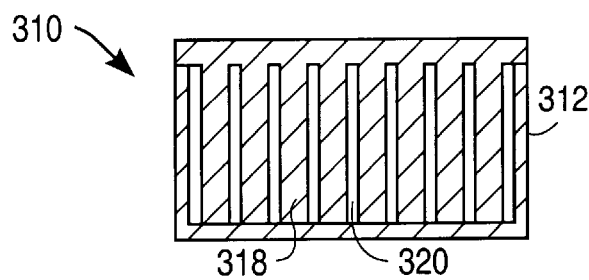 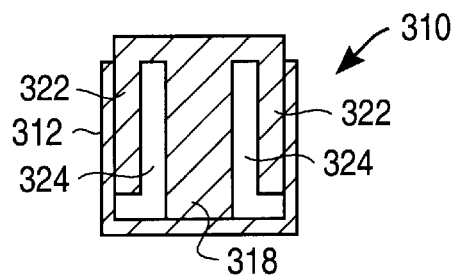
FIG. 12b(i)    FIG. 12b(ii)
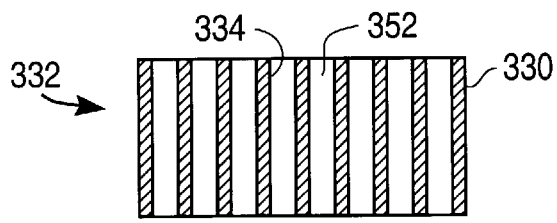 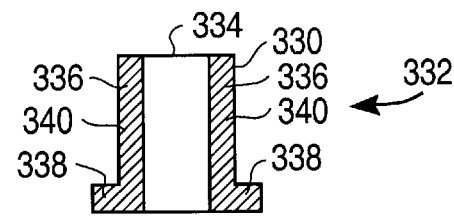
FIG. 12c(i)    FIG. 12c(ii)
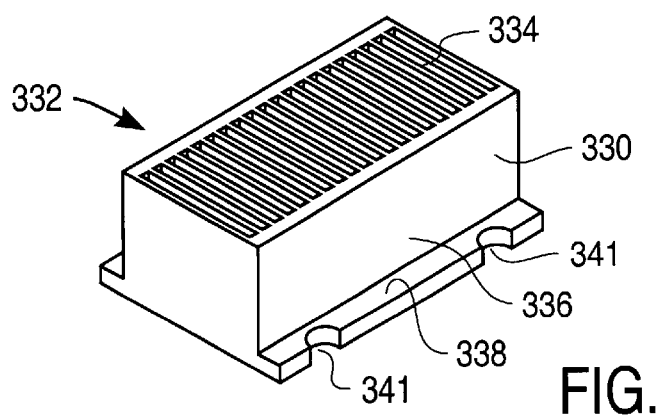
FIG. 13

NONINTRUSIVE INSPECTION SYSTEM

CROSS-REFERENCE TO RELATED APPLICATIONS

This is a continuation of PCT/US99/28229 filed on Nov. 29, 1999, which claims priority from U.S. Provisional Patent Application No. 60/110,417 filed on Nov. 30, 1998.

BACKGROUND TO THE INVENTION

1.) Field of the Invention

This invention relates to an x-ray technique-based nonintrusive inspection apparatus. An x-ray technique-based nonintrusive inspection apparatus according to the invention may, for example, be used for nonintrusively inspecting closed containers before being loaded into a loading bay of an aircraft, or may include technologies which may find application in other similar or different inspection apparatus.

2.) Discussion of Related Art

Inspection apparatus are commonly used for nonintrusively inspecting luggage and other closed containers before being loaded into a loading bay of an aircraft. Older generation inspection apparatus relied merely on conventional x-ray technology for nonintrusively inspecting closed containers. More recently, inspection apparatus which rely on computer tomography (CT) scanning technology have also been utilized. An inspection apparatus utilizing CT scanning technology is described in U.S. Pat. Nos. 5,182,764 and 5,367,552 by Peschmann et al. which are assigned to the assignee of the present case and which are hereby incorporated by reference.

SUMMARY OF THE INVENTION

The invention provides an x-ray technique-based nonintrusive inspection apparatus which allows for "radiation locking" as will be described in more detail in the description that follows. The inspection apparatus includes loading inspection and unloading tunnel sections, first, second and third conveyor apparatus, an x-ray source, first, second, third and fourth actuation devices, and first, second, third and fourth radiation resistant closure members.

Each tunnel section has a respective first end and a respective second end opposing the first end thereof. The inspection tunnel section is located in line after the loading tunnel section so that the second end of the loading tunnel section is adjacent the first end of the inspection tunnel section. The unloading tunnel section is located in line after the inspection tunnel section so that the second end of the inspection tunnel section is located adjacent the first end of the unloading tunnel section.

The first conveyor apparatus has at least one conveyor belt which is at least partially located within the loading tunnel section and which, upon movement, is capable of moving an object from the first end of the loading tunnel section to the second end of the loading tunnel section. The second conveyor apparatus has at least one conveyor belt which is at least partially located within the inspection tunnel section and which, upon movement, is capable of moving an object from the first end of the inspection tunnel section to the second end of the inspection tunnel section. The third conveyor apparatus has at least one conveyor belt which is at least partially located within the unloading tunnel section and which, upon movement, is capable of moving an object from the first end of the unloading tunnel section to the second end of the unloading tunnel section.

The x-ray source, when operated, creates radiation within the inspection tunnel section.

The first closure member is movable by the first actuation device between an open position wherein the first end of the loading tunnel section is open, and a closed position wherein the first closure member closes the first end of the loading tunnel section. The second closure member is movable by the second actuation device between an open position wherein the second end of the loading tunnel section is in communication with the first end of the inspection tunnel section to allow for movement of an object from the loading tunnel section to the inspection tunnel section, and a closed position wherein the second closure member substantially closes off communication between the first and inspection tunnel sections. The third closure member is movable by the third actuation device between an open position wherein the second end of the inspection tunnel section is in communication with the first end of the unloading tunnel section to allow for movement of an object from the inspection tunnel section to the unloading tunnel section, and a closed position wherein the third closure member substantially closes off communication between the second and unloading tunnel sections. The fourth closure member is movable by the fourth actuation device between an open position wherein the second end of the loading tunnel section is open, and a closed position wherein the fourth closure member closes the second end of the unloading tunnel section.

The inspection apparatus may further include first, second, third and fourth curtain rollers, each being rotatable by a respective one of the actuation devices. The closure members may be curtains and each curtain may be secured to a respective curtain roller so as to be rolled onto or from the curtain roller upon rotation of the curtain roller.

The inspection apparatus may further include a controller which controls power supplied to the respective actuation devices. The controller may be programmed to synchronize the actuation devices so that, at least when the x-ray source creates radiation within the inspection tunnel section, at least one of the first and second closure members is in its respective closed position and at least one of the third and fourth closure members is in its respective closed position. The controller may turn the radiation source off when both the first and second closure members are not entirely in their respective closed positions, or when both the third and fourth closure members are not entirely in their respective closed positions.

The invention also provides a method of nonintrusively inspecting an object in a "radiation locking" manner, utilizing an x-ray technique-based nonintrusive inspection apparatus, that permits x-rays generated in an inspection tunnel section thereof to remain on continuously. A first radiation resistant closure member is moved into an open position wherein a first end of a loading tunnel section is open, while a second radiation resistant closure member is in a closed position wherein it closes a second end of the loading tunnel section opposing the first end of the loading tunnel section. An object is moved through the first end of the loading tunnel section into the loading tunnel section while the second closure member remains in its closed position. The first closure member is then moved into a closed position wherein the first closure member closes the first end of the first tunnel. After movement of the first closure member into its closed position, the second closure member is moved into an open position wherein the second end of the loading tunnel section is in communication with a first end of a inspection tunnel section. The object is then moved from the loading tunnel section into the inspection tunnel section. After movement of the object into the inspection tunnel section, the second closure member is moved into its closed position so as to substantially close off communication between the first and inspection tunnel sections. The object is then radiated within the inspection tunnel section.

The confines of the inspection tunnel section may be radiated while the object is moved into the loading tunnel section.

The first closure member may remain in its closed position while the object is moved into the inspection tunnel section. The confines of the inspection tunnel section may be radiated while the object is moved into the inspection tunnel section.

The invention also provides a method of nonintrusively inspecting an object by simultaneously utilizing an x-ray line scanner subsystem and a CT scanner subsystem, in an x-ray technique-based nonintrusive inspection apparatus, which may be in a close relationship relative to one another. A front portion of the object is first scanned utilizing the x-ray line scanner subsystem. A section within the front portion of the object is scanned utilizing a CT scanner subsystem. A rear portion of the object is then scanned, utilizing the x-ray line scanner subsystem, after the section in the front portion is scanned utilizing the CT scanner subsystem.

The object may, for example, be a closed container which is nonintrusively inspected.

The object may be scanned while being moved relative to the x-ray line scanner subsystem and the CT scanner subsystem, and the front portion and the rear portion may be scanned without altering the direction of movement of the object relative to the x-ray line scanner subsystem and the CT scanner subsystem, although it may be necessary to bring the object to a halt relative to the CT scanner subsystem. Movement of the object relative to the x-ray line scanner subsystem and the CT scanner subsystem may be progressively reduced after the section is scanned by the x-ray line scanner subsystem but before the section is scanned by the CT scanner subsystem.

The invention also provides an x-ray technique-based nonintrusive inspection apparatus having both x-ray and CT scanning capabilities within a single tunnel section. The inspection apparatus includes at least one tunnel section, a conveyor apparatus, an x-ray line scanner subsystem, and a CT scanner subsystem. The tunnel section has first and second opposed ends. The conveyor apparatus has at least one conveyor belt which is at least partially located within the tunnel section. The conveyor belt, upon movement, is capable of transporting an object from the first end to the second end of the tunnel section. The x-ray line scanner subsystem is positioned to scan at a first plane within the tunnel section. The CT scanner subsystem is positioned to scan at a second plane within the tunnel section.

The first and second planes may be located by distance of less than 110 centimeters from one another.

Preferably, the same conveyor belt conveys the object from the first plane to the second plane.

The inspection apparatus may further include a base frame, and a support structure having a lower end secured to the base frame and extending upwardly therefrom, and the x-ray line scanner subsystem and the CT scanner subsystem may both the mounted to the support structure.

The invention also provides an x-ray technique-based nonintrusive inspection apparatus having good structural integrity. The inspection apparatus includes a base frame of monocoque design, a support structure, and a CT scanner subsystem. The support structure is secured to the base frame. The CT scanner subsystem is rotatably mounted to the support structure. Although having specific application for x-ray technique-based nonintrusive inspection apparatus used for detecting contraband in closed containers, inspection apparatus are also envisioned having base frames of monocoque design which are not necessarily used for the detection of contraband within closed containers.

A motor may be coupled to the CT scanner subsystem so as to rotate the CT scanner subsystem, for example at a rate of at least 100 revolutions per minute.

The CT scanner subsystem may define an opening having a cross-dimension of at least 110 centimeters.

The CT scanner subsystem may define an opening and the inspection apparatus may further include a conveyor apparatus mounted to the base frame. The conveyor apparatus may have a conveyor belt which passes through the opening. The conveyor belt may have a width of at least 90 cm.

The CT scanner subsystem may include a gantry enclosure, a radiation source mounted on one side to the gantry enclosure so that, when the radiation source is operated, the confines of the gantry enclosure are radiated, the gantry enclosure being at least partially made of lead.

The invention also provides a CT scanner subsystem of a nonintrusive inspection system which is at least partially self shielded so as to attenuate leaking of radiation therefrom to acceptable levels. The CT scanner subsystem may include first and second spaced gantry plates, at least one spacer, a ring, and an x-ray source. The first and second gantry plates each have a respective gantry aperture formed therein. The at least one spacer is located between the gantry plates so that the at least one spacer together with the gantry plates define a partial gantry enclosure. The ring is located on the gantry enclosure and allows the gantry enclosure to be mounted to a support structure for rotation about an axis through the gantry apertures. The x-ray source is secured to the gantry enclosure at one side thereof so that, when the x-ray source is operated, the confines of the gantry enclosure are at least partially radiated. The gantry enclosure is at least partially made of a material which substantially attenuates radiation leakage from the gantry enclosure i.e. by a degree which is much more than for example attenuation of radiation with steel. The gantry enclosure may for example include a liner of lead or another material which, substantially attenuates radiation leakage on the first or second gantry plates or on the spacer. The x-ray source may include an x-ray tube and a liner, of lead or another material which substantially attenuates radiation leakage, on the x-ray tube.

The invention also provides an x-ray technique-based noninstrusive inspection apparatus including a support frame, a CT scanner subsystem, and a tunnel portion. The CT scanner subsystem may include first and second spaced gantry plates, at least one spacer, and an x-ray source. Each gantry plate may have a respective gantry aperture formed therein. The at least one spacer may be located between the gantry plates so that the at least one spacer together with the gantry plates define a partial gantry enclosure. The x-ray source may be secured to the gantry enclosure at one side thereof so that, when the x-ray source is operated, the confines of the gantry enclosure are at least partially radiated. The gantry enclosure is at least partially made of a material which substantially attenuates radiation leakage from the gantry enclosure. The CT scanner subsystem is mounted to the support frame for rotation about an axis through the first and second gantry apertures. The tunnel portion is nonrotatably mounted to the support frame and has an end which mates with the gantry aperture in the first gantry plate. The tunnel portion is also at least partially made of a material which substantially attenuates radiation leakage from the tunnel portion.

The invention also provides an x-ray technique-based nonintrusive inspection apparatus which is easily maintainable because of the location of a flexible member such as a belt or a chain which is used for driving a CT scanner subsystem of the inspection apparatus. The inspection apparatus includes a support frame, a CT scanner subsystem, at least first, second and third pulleys, and a flexible member. The CT scanner subsystem is rotatably mounted to the support frame and has a circular outer surface. The first, second and third pulleys are mounted around the CT scanner subsystem to the support frame. The flexible member runs over the first, second and third pulleys. A first section of the flexible member runs from the first pulley to the second pulley in a first direction around and over the circular outer surface. A second section of the flexible member returns from the second pulley over the third pulley back to the first pulley in a second direction, opposite to the first direction, around the circular outer surface.

According to one aspect of the invention, an x-ray technique-based nonintrusive inspection apparatus is provided including at least a first tunnel section, an x-ray source, at least a first actuation device, and at least a first radiation resistant closure member. The first tunnel section has first and second opposed ends. The x-ray source, when operated, creates radiation within the first tunnel section. The first radiation resistant closure member is movable by the actuation device between an open position wherein the first end of the first tunnel section is open, and a closed position wherein the first closure member closes the first end of the first tunnel section. The inspection apparatus thus has an "active" closure member. Specific advantages of active closure members are discussed in the description that follows.

The inspection apparatus may include a tensioning roller which is rotatably mounted to the support frame. The tensioning roller acts on the curtain and tends to roll the curtain from the curtain roller.

The inspection apparatus may further include a spring which is biased between the support frame and the tensioning roller so as to tend to rotate the tensioning roller.

The inspection apparatus may further include a sheet which has a first portion attached to the curtain roller and a second portion attached to the tensioning roller, so as to connect the tensioning roller to the curtain. The sheet may be secured to the curtain roller without intervention by the curtain.

The curtain preferably hangs from one side of the curtain roller and the tensioning roller is preferably located on the same side of the curtain roller as the side of the curtain roller from which the curtain hangs.

The invention also provides an effective manner of making a collimator for a detector array of the x-ray detection apparatus. First, a die is injected with a material. The material is then allowed to set within the die to form a body. The body is then removed from the die. The body typically includes a support structure and a plurality of septa secured to the support structure.

The material preferably includes a first, lead component comprising at least 90 percent thereof. The material may include a second component which is stronger than lead. The second component may, for example, include tin.

According to the method, a collimator for a detector array may be formed wherein septa of the collimator converge.

The collimator may include a body which includes a support structure and a plurality of septa secured to the support structure. Center lines of two of the septa located next to one another converge in a first direction so that the septa may be aligned with a radiation source, but surfaces of the two septa facing one another do not converge in the first direction so as to allow for removal of the body from a die which is used to form the body.

The invention also provides a collimator for a detector array of an x-ray inspection apparatus, which includes a body which includes at least one support structure and a plurality of septa secured to the support structure. The body is made of a material having a first, lead component comprising at least 90 percent thereof.

For added strength, the body may include first and second support structures with the septa secured between the first and second support structures.

The invention also provides a collimator for a detector array of an x-ray inspection apparatus which allows for modular design of detector arrays. The collimator includes a body having a plurality of registration formations thereon. The body includes a support structure and a plurality of septa secured to the support structure.

Each registration formation may be a respective notch in a portion of the body.

The invention also provides an x-ray technique-based nonintrusive inspection apparatus which allows for easy release of parts of containers which become jammed between rollers of conveyor apparatus which are located sequentially one after the other. The inspection apparatus includes a base frame, a tunnel section, a conveyor belt mounting structure, front and rear conveyor rollers, and a conveyor belt. The tunnel section has a first end and a second end opposing the first end, and is mounted to the base frame. The front and rear rollers are rotatably mounted to the conveyor belt mounting structure. The conveyor belt runs over the front and rear conveyor rollers. The conveyor belt mounting structure is mounted to the base frame for at least limited movement, between first and second positions, in a direction in which the conveyor belt moves between the front and rear conveyor rollers. The conveyor belt extends at least some distance between the first and second ends through the tunnel section.

The invention also extends to a method of assembling an x-ray technique-based nonintrusive inspection apparatus wherein a conveyor belt of the inspection apparatus is preinstalled and wherein the conveyor belt may be pretensioned. A conveyor belt mounting structure, having front and rear conveyor rollers rotatably mounted thereto, and a conveyor belt over the front and rear conveyor rollers, is mounted to a base frame. The conveyor belt mounting structure is mounted to the base frame for at least limited movement between first and second positions in a direction in which the conveyor belt moves over the front and rear conveyor rollers.

The invention also provides an x-ray technique-based nonintrusive inspection apparatus having a housing which is designed, for purposes of keeping contaminants from entering the housing, to have a higher pressure inside the housing than externally of the housing. The nonintrusive inspection apparatus includes a base frame, tunneling, an x-ray source, paneling, and a fan. The tunneling is mounted to the base frame and has a first end and a second end opposing the first end. The x-ray source which, when operated, creates radiation within the tunneling. The paneling is located around the tunneling and the x-ray source so that the paneling and the base frame jointly define a housing around the tunneling and the x-ray source. The housing has an entry aperture in proximity to the first end, and an exit aperture in proximity to the second end of the tunneling. The housing also has an air inlet opening. The fan is positioned to draw air through the inlet opening into the housing. The housing is formed, the entry aperture seals with the first end of the tunneling to an extent sufficient, and the exit aperture seals with the second end of the tunneling to an extent sufficient so that the confines of the housing are at a higher pressure than externally of the housing when the fan draws into the housing.

The invention also provides an x-ray technique-based nonintrusive inspection apparatus which may be cooled without necessarily having a fan mounted to a rotating gantry enclosure thereof. The nonintrusive inspection apparatus includes a support frame, a CT scanner subsystem, a plenum, an air-conditioning unit, and a duct. The CT scanner subsystem is rotatably mounted to the support frame and has a gantry enclosure. At least one air passage is formed into the gantry enclosure. The plenum is nonrotatably mounted to the support frame. The plenum is located externally of the gantry enclosure over the air passage so that the confines of the plenum are in communication with the air passage. The air-conditioning unit includes a fan. The duct connects the air-conditioning unit with the plenum. When the fan is operated, air passes from the air-conditioning unit through the duct to the plenum, from the plenum through the air passage into the gantry enclosure, and from the gantry enclosure through the radiator.

BRIEF DESCRIPTION OF THE DRAWINGS

The invention is further described by way of example with reference to the accompanying drawings wherein like reference numerals indicate like or similar components and wherein:

FIG. 4a(ii) is a plan view of the container in FIG. 4a(i);

FIG. 4b(ii) is a plan view of the container in FIG. 4b(i);

FIG. 4c(ii) is a plan view of the container in FIG. 4c(i);

FIG. 6 is a cross-sectional side view which illustrates how radiation is shielded within the inspection tunnel section;

FIG. 12a(i) is a cross-sectional side view of a die which is used to form a detector array collimator of the inspection apparatus, illustrating the die in exploded form;

FIG. 12a(ii) is a cross-sectional end view of the die of FIG. 12a(i);

FIG. 12b(i) is a view similar to FIG. 12a(i) after the die is assembled and before a material is injected into the die;

FIG. 12b(ii) is a cross-sectional end view of the die in FIG. 12 b(i);

FIG. 12c(i) is a cross-sectional view of a detector array collimator which is formed by injecting a material into the die of FIG. 12b(i);

FIG. 12c(ii) is a cross-sectional end view of the detector array collimator of FIG. 12c(i);

FIG. 13 is a perspective view of the detector array collimator of FIG. 11c(i) and FIG. 11c(ii);

DESCRIPTION OF THE INVENTION

Introductory Description

Figure 1:
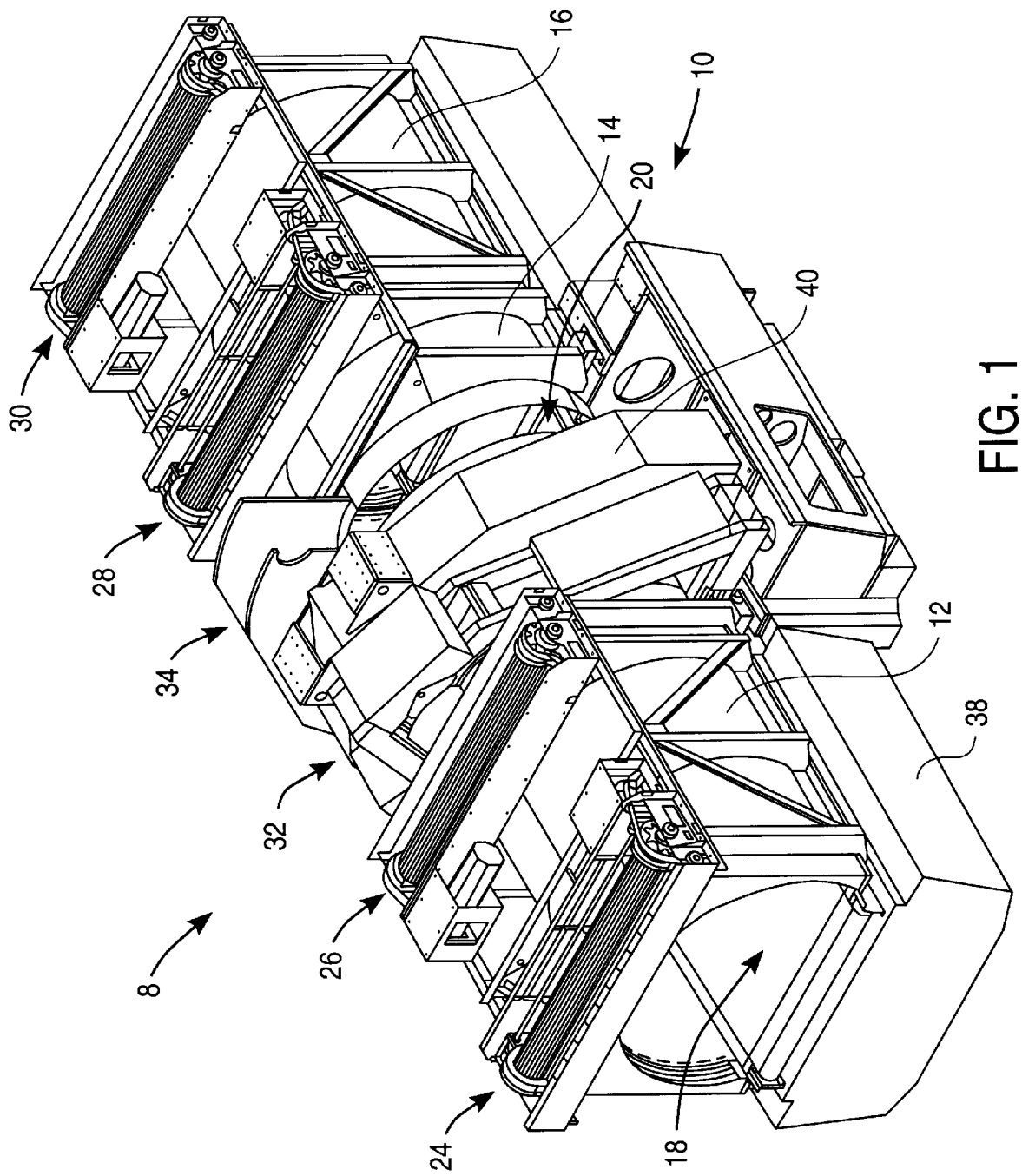
FIG. 1 is a perspective view of an x-ray technique-based nonintrusive inspection apparatus according to an embodiment of the invention.
Figure 2:
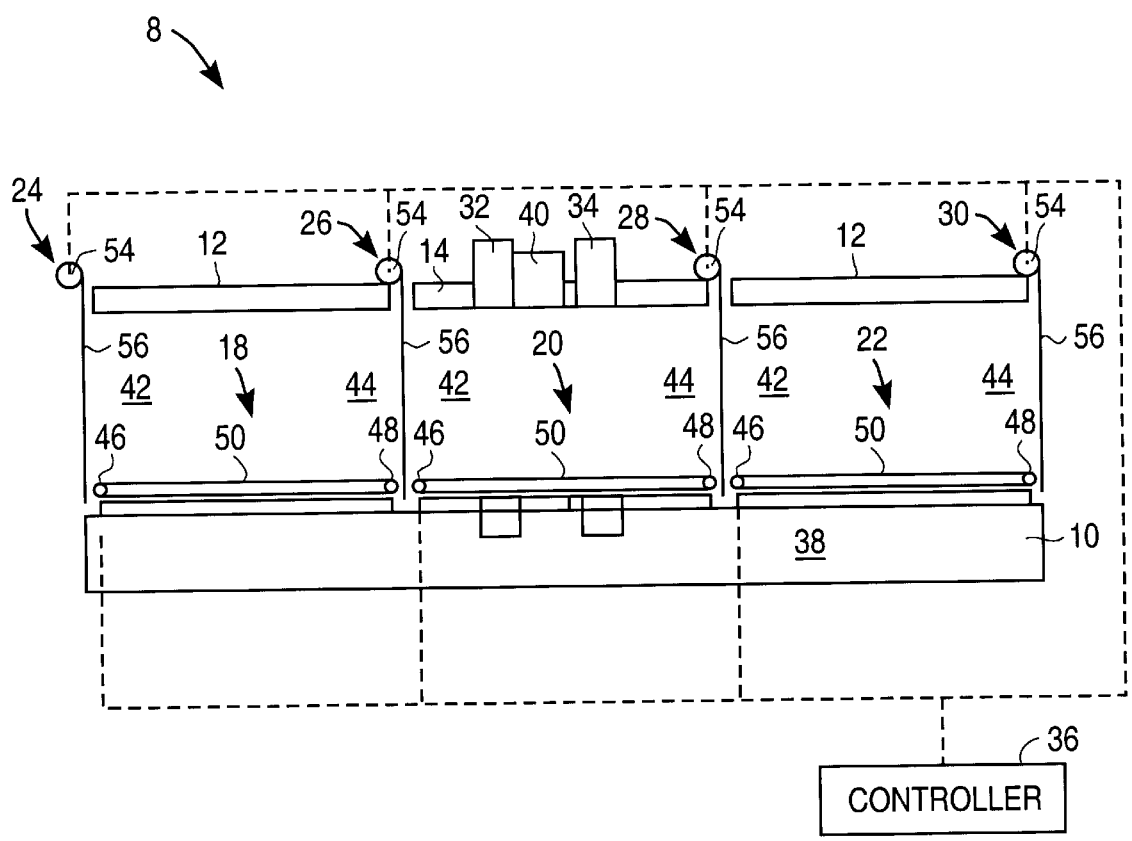
FIG. 2 is a cross-sectional side view representing some of the components of the inspection apparatus of FIG. 1.

FIG. 1 and FIG. 2 of the accompanying drawings illustrate an x-ray technique-based nonintrusive inspection apparatus 8 according to an embodiment of the invention. The inspection apparatus 8 includes a support frame 10, a loading tunnel section 12, an inspection tunnel section 14, an unloading tunnel section 16, a loading conveyor apparatus 18, and inspection conveyor apparatus 20, an unloading conveyor apparatus 22, first, second, third and fourth shielding arrangements, 24, 26, 28 and 30 respectively, a stationary x-ray line scanner subsystem 32, a rotating CT scanner subsystem 34, and a controller 36.

The support frame 10 includes a base frame 38 and an arch 40 which arches in a plane perpendicular to the drawing and which is secured to the base frame 38 on opposing sides of the arch 40. The x-ray line scanner subsystem 32 is mounted on one side of the arch 40 and the CT scanner subsystem 34 is mounted to the arch 40 for rotation in a plane perpendicular to the drawing on a side of the arch 40 opposing the x-ray line scanner subsystem 32.

Referring now in particular to FIG. 2, each tunnel section 12, 14 or 16 has a respective first end 42 and a respective second end 44 opposing the first end thereof. The inspection tunnel section 14 is located in line after the loading tunnel section 12 so that the second end 44 of the loading tunnel section 12 is adjacent the first end 42 of the inspection tunnel section 14. The unloading tunnel section 16 is located in line after the inspection tunnel section 14 so that the second end 44 of the inspection tunnel section 14 is located adjacent the first end 42 of the unloading tunnel section 16. All the tunnel sections 12, 14 and 16 are mounted to the base frame 38.

Each conveyor apparatus 18, 20 or 22 is located within a respective tunnel section 12, 14 or 16. Each conveyor apparatus 18, 20 or 22 includes a respective front conveyor roller 46 near a respective first end 42 of a respective tunnel section 12, 14 or 16, a respective rear conveyor roller 48 near a respective second end 44 of a respective tunnel section 12, 14 or 16, and a conveyor belt 50 which runs over the conveyor rollers 46 and 48 and a supporting bed (not shown). Although not shown in FIG. 2 so as not to obscure the drawing, it should be understood that each conveyor roller 46 and 48 of each conveyor apparatus 18, 20 and 22 is rotatably mounted to a respective bracket assembly and that each bracket assembly is secured to the base frame 38. It should also be understood that one of the conveyor rollers 46 or 48 of each conveyor apparatus 18, 20 and 22 is rotated by a respective motor which is mounted to the base frame 38 but which is not shown in FIG. 2 so as not to obscure the drawing.

Each shielding arrangement 24, 26, 28 and 30 includes a respective curtain roller 54 and a respective radiation resistant curtain 56 secured to the curtain roller 54. Although not shown in FIG. 2 so as not to obscure the drawing, it should be understood that each curtain roller 54 is rotatably mounted to a respective support structure and that each support structure is secured to the base frame 38. It should also be understood that each curtain roller 54 is rotated by a respective motor which may also be mounted to the support structure but which is not shown in FIG. 2 so as not to obscure the drawing. The curtain rollers 54 are positioned so that each curtain 56 is located near an end 42 or 44 of one or more of the tunnel sections 12, 14 and 16.

Rotation of the curtain roller 54 in one direction causes the curtain 56 to be rolled from the curtain roller 54 which causes the curtain 56 to drop, and rotation of the curtain roller 54 in an opposite direction raises the curtain 56 by rolling the curtain 56 onto the curtain roller 54.

When the curtain 56 is raised, the curtain 56 is moved into an open position wherein the end or ends 42 or 44 are open, and when the curtain is dropped the curtain is moved into a "closed position" wherein the curtain 56 closes the end or ends 42 or 44.

For example, when the curtain 56 of the first shielding arrangement 24 is moved into its open position, the first end 42 of the loading tunnel section 12 is open, and when the curtain 56 of the first shielding arrangement 24 is moved into its closed position, the first end 42 of the loading tunnel section 12 is closed.

Similarly, when the curtain 56 of the second shielding arrangement 26 is moved into its open position, the second end 44 of the loading tunnel section 12 is in communication with the first end 42 of the inspection tunnel section 14, and when the curtain 56 of the second shielding arrangement 26 is moved into its open position, communication between the loading and inspection tunnel sections 12 and 14 is substantially closed off.

Similarly, when the curtain 56 of the third shielding arrangement 28 is moved into its open position, the second end 44 of the inspection tunnel section 14 is in communication with the first end 42 of the unloading tunnel section 16, and when the curtain 56 of the third screening arrangement 28 is moved into its closed position, communication between the inspection and unloading tunnel sections 14 and 16 is substantially closed off.

Similarly, when the curtain 56 of the fourth shielding arrangement 30 is moved into its open position, the second end 44 of the unloading tunnel section 16 is open, and when the curtain 56 of the fourth shielding arrangement 30 is moved into its closed position, the second end 44 of the unloading tunnel section 16 is closed.

Detectors (not shown) are positioned to detect the positioning of each curtain 56 independently. More detectors (not shown) are positioned to detect the positioning, speed and acceleration of each conveyor belt 50 independently. More detectors (not shown) are positioned to detect the positioning of containers at various locations within the inspection apparatus 8.

The controller 36 is in communication with the detectors. A disk or other computer readable medium may be provided on which an executable program is stored. The controller 36 may, for example, be a computer which is capable of reading the program on the disk and may include memory in the program is stored. The program, once executed may automatically synchronize movement of the curtains 56 and the conveyor belts 50 in a manner which is generally referred to as "radiation locking". Radiation locking is further described hereinbelow with reference to FIG. 3a to FIG. 3j. The controller 36 also controls other aspects of movement of containers through the inspection apparatus 8 which are further described hereinbelow with reference to FIG. 4a(i) to FIG. 4c(ii). It can generally be noted that this stage that radiation locking provides adequate shielding of x-ray radiation from people that may be located in an area around the inspection apparatus 8. The controller 36 controls power supplied to the motors which drive the conveyor apparatus 18, 20 and 22 so as to control the positioning, speed and acceleration of the conveyor belts 50 of the conveyor apparatus 18, 20 and 22. The controller 36 also controls power supplied to the motors which drive the curtain rollers 54 of the first, second and third shielding arrangement 24, 26, 28 and 30 so as to control the positioning, speed and acceleration of the curtain rollers 54 of the first, second and third shielding arrangement 24, 26, 28 and 30.

One advantage of the inspection apparatus 8 illustrated in FIG. 2 is that, because of adequate shielding due to radiation locking, there is no need for locating the conveyor apparatus 18, 20 and 22 so that they define an elaborate undulating path—the conveyor belts 50 are all linearly aligned with one another, and are located within the same horizontal plane (if, of course, the inspection apparatus 8 is located on a horizontal floor). When a technician has to enter any one of the tunnel sections 12, 14 or 16, the technician may easily enter the tunnel section without the need for the technician to climb up an inclined conveyor apparatus, as is often the case in certain prior art apparatus.

A further advantage of the fact that the conveyor belts 50 are all linearly aligned is that the height of the overall apparatus can be minimized. In one example the inspection apparatus 8, ones enclosed by a housing, has an overall height of about 223 centimeters. A further advantage is that the maximum speed of objects passing through the inspection apparatus 8 is not constrained by the existence of discontinuities in the belt path.

A further advantage of the inspection apparatus 8 is that the curtains 56 are "active curtains" in the sense that each curtain 56 opens to allow for a container to pass 56 without obstruction by the curtain 56. The curtain 56 does therefore not create a volume of "dead space" by lying on top of the container. Larger objects can therefore be moved into a respective tunnel section 12, 14 or 16 although each conveyor apparatus 18, 20 or 22 may have a smaller footprint. Larger containers are typically about 110 centimeters in length and in one example the loading tunnel section 12 has a length of about 135 centimeters and the unloading tunnel 16 has a length of about 135 centimeters. Because dead space is minimized, the overall length of the apparatus is thus decreased. Active curtains also have the advantage that they may allow for passing through of heavier containers, which may for example be as much as one meter in height, but that very light weight containers may also pass through without being obstructed, there being no absolute minimum weight requirement for passing through the active curtains. Larger light objects in particular may pass through easier than through prior art passive curtains.

It should also be noted that the x-ray line scanner subsystem 32 and the CT scanner subsystem 34 operate within the same tunnel section, namely the inspection tunnel section 14, without an intermediate radiation resistant curtain or other shielding device. By locating the x-ray line scanner subsystem 32 and the CT. scanner subsystem 34 within the same tunnel section, the overall length of the inspection apparatus 8 is reduced. As will be described in more detail hereinbelow, collimators prevent, or limit, interference between x-rays of the x-ray line scanner subsystem 32 and the CT. scanner subsystem 34.

Furthermore, it should be noted that the x-ray line scanner subsystem 32 and the CT scanner subsystem 34 are both mounted to the same upwardly extending support structure, namely the arch 40. By mounting the x-ray line scanner subsystem 32 and the CT scanner subsystem 34 both to the same support structure, the orientation of the x-ray line scanner subsystem 32 and the CT scanner subsystem 34 relative to one another can be more accurately controlled. In particular, the x-ray line scanner subsystem 32 may scan in a first plane and the CT scanner subsystem 34 may scan in a second plane which is parallel to the first plane to a much tighter tolerance. Parallelism between the first and second planes is important because it greatly reduces the complexity of software used for coordinating images received from the x-ray line scanner subsystem 32 and the CT scanner subsystem 34.

It should also be noted that the same conveyor belt, namely the conveyor belt 50 of the inspection conveyor apparatus 20, transports containers while being scanned respectively by the x-ray line scanner subsystem 32 and the CT scanner subsystem 34. There is thus no transition from one conveyor belt to another between the x-ray line scanner subsystem 32 and the CT scanner subsystem 34. Because of the use of a single conveyor belt for transporting containers from the x-ray line scanner subsystem 32 to the CT scanner subsystem 34, the orientation and predictability of positioning of the containers are insured.

As will also be evident from the description that follows, many features of the inspection apparatus 8 provide for high speed inspection of containers. The features providing for high speed inspection of containers in combination generally make provision for inspection of at least 600 containers per hour.

Radiation Locking

The concept of radiation locking is now described by way of an example illustrated in FIG. 3a to FIG. 3j.

In the description that follows, the curtain of the first shielding arrangement 24 is referred to as "the first curtain 56A", the curtain of the second shielding arrangement 26 is referred to as "the second curtain 56B" the curtain of the third shielding arrangement 28 is referred to as "the third curtain 56C", and the curtain of the fourth shielding arrangement 30 is referred to as "the fourth curtain 56D". (Compare FIG. 2 with FIG. 3a).

In the following discussion of FIG. 3a to FIG. 3j it can also be inferred that the confines of the inspection tunnel section 14 are continuously radiated, unless specifically stated otherwise.

Figure 3:
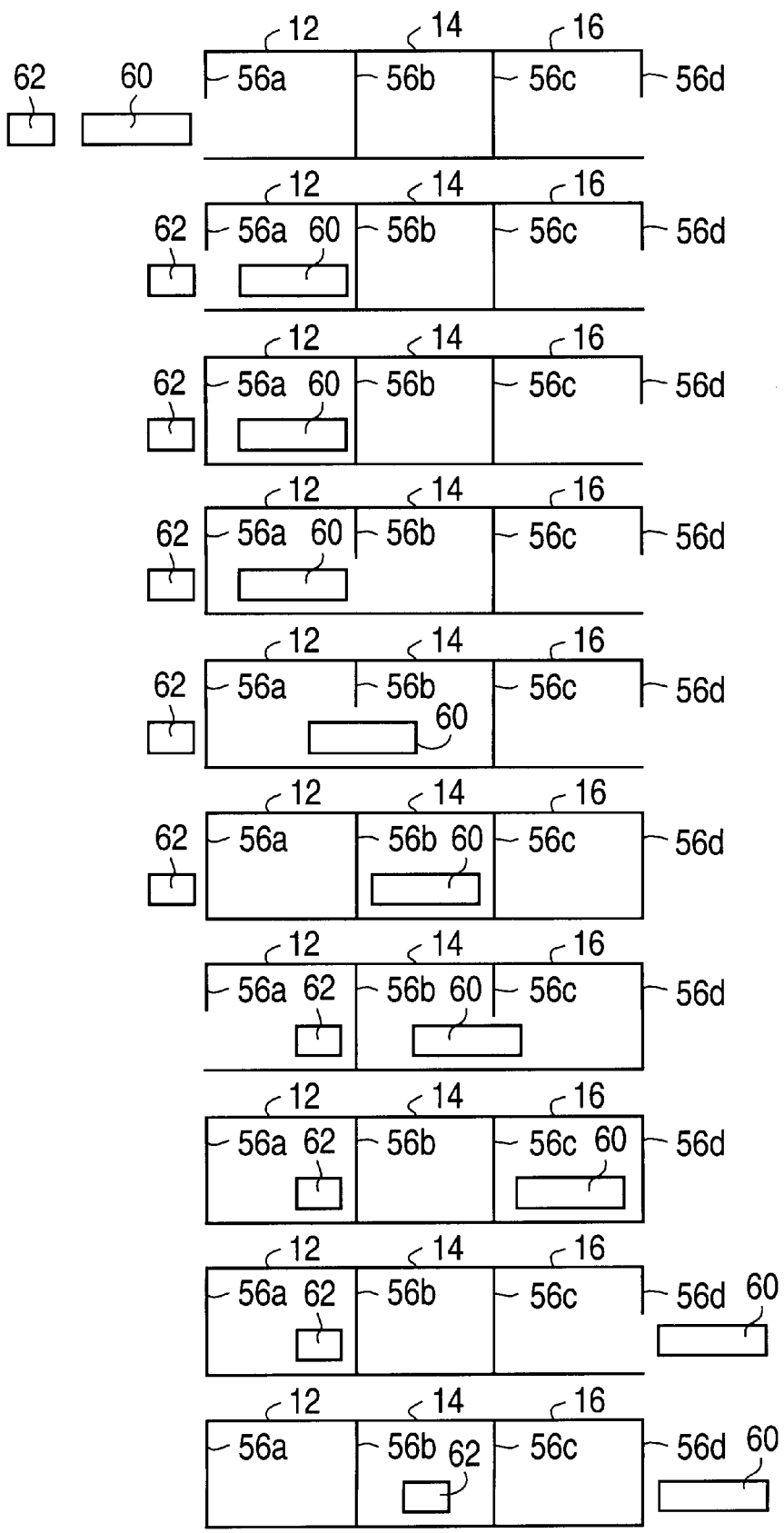
FIG. 3a is a side view representing the inspection apparatus of FIG. 2 before a first container and a second container are moved into a loading tunnel section of the inspection apparatus.
FIG. 3b is a view similar to FIG. 3a after the first container is moved into the loading tunnel section.
FIG. 3c is a view similar to FIG. 3b after a first radiation resistant curtain is closed behind the first container.
FIG. 3d is a view similar to FIG. 3c after a second radiation resistant curtain in front of the first container is opened.
FIG. 3e is a view similar to FIG. 3d while the first container is moved into and inspection tunnel section of the inspection apparatus.
FIG. 3f is a view similar to FIG. 3e after the first container is located entirely within the inspection tunnel section and the second radiation resistant curtain is closed behind the first container.
FIG. 3g is a view similar to FIG. 3f after a third radiation resistant curtain in front of the first container is opened and while the first container is moved into an unloading tunnel section of the inspection apparatus, and after the second container is moved into the loading tunnel section.
FIG. 3h is a view similar to FIG. 3g after the first container is located entirely within the unloading tunnel section and the third radiation resistant curtain is closed behind the first container, and after the first radiation resistant curtain is closed behind the second container.
FIG. 3i is a view similar to FIG. 3h after a fourth radiation resistant curtain in front of the first container is opened and the first container is moved out of the unloading tunnel section, and after the second radiation resistant curtain is opened in front of the second container.
FIG. 3j is a view similar to FIG. 3i after the fourth radiation resistant curtain is closed behind the first container, after the second container is moved into the inspection tunnel section, and after the second radiation resistant curtain is closed behind the second container.

First, as illustrated in FIG. 3a, a number of closed containers 60, 62 are lined up, utilizing conventional airport conveyor belts, in front of the first curtain 56A. The first curtain 56A is raised. The second curtain 56B remains in a down position so that radiation from the inspection tunnel section 14 is prevented from reaching the loading tunnel section 12.

Next, as illustrated in FIG. 3b, a first of the containers 60 is moved through the first end of the loading tunnel section 12 into the loading tunnel section 12. The second curtain 56B remains in a down position.

Next, as illustrated in FIG. 3c, the first curtain 56A is lowered, thus "locking" the first container 60 between the first curtain 56A and the second curtain 56B and hence the concept of "radiation locking". Radiation locking merely serves to ensure that the first curtain 56A is down before the second curtain 56B is raised and generally lasts only for a fraction of a second.

Next, as illustrated in FIG. 3d, the second curtain 56B is raised. Although radiation from the inspection tunnel section 14 may enter the loading tunnel section 12, the radiation is prevented by the first curtain 56A from leaving the loading tunnel section 12.

It can already be seen from the discussions of FIG. 3a to FIG. 3d that at least one of the first curtain 56A and the second curtain 56B is always in a down position, at least when the confines of the inspection tunnel section 14 are radiated. Radiation is therefore prevented from leaving the inspection apparatus from a container entry side. The controller (see reference numeral 36 in FIG. 2) may be programmed so that the line scanner 32 and the CT scanner subsystem 34 are switched off when, for whatever reason, both the first curtain 56A and the second curtain 56B are at least partially open (or when both the first curtain 56A and the second curtain 56B are not entirely closed). Sensors may for example be provided which detect the positioning of the curtains 56A and 56B and which forward the detected information to the controller.

Next, as illustrated in FIG. 3e, the first container 60 is moved (utilizing the first and second conveyor apparatus 18 and 20—see FIG. 2) from the loading tunnel section 12 into the inspection tunnel section 14.

Once the first container 60 is located entirely within the inspection tunnel section 14, the second curtain 56B is again lowered, as illustrated in FIG. 3f.

Next, as illustrated in FIG. 3g, the third curtain 56C is raised and the first container 60 is moved (utilizing the second and third conveyor apparatus 20 and 22—see FIG. 2) from the inspection tunnel section 14 into the unloading tunnel section 16. The fourth curtain 56D remains in a down position so as to prevent radiation, which may enter the unloading tunnel section 16 from the inspection tunnel section 14, from leaving the inspection apparatus through the second end of the unloading tunnel section 16.

In the meantime, a second of the containers 62 may be moved into the loading tunnel section 12 in a manner as hereinbefore described with reference to FIG. 3a to FIG. 3d. Further movement of the second container 62 is similar to the movement of the first container 60 as hereinbefore and hereinafter described and should further be evident from the drawings.

Once the first container 60 is located entirely within the unloading tunnel section 16, the third curtain 56C is again lowered, as illustrated in FIG. 3h. The first container 60 is thus locked between the third curtain 56C and the fourth curtain 56D, again illustrating the concept of radiation locking, this time after exit of the first container 60 from the inspection tunnel section 14. Again, radiation locking of the first container 60 within the unloading tunnel section 16 may last only for a fraction of a second.

As with the first and second curtains 56A and 56B, at least one of the third curtain 56C and the fourth curtain 56D is always in a down position, at least when the confines of the inspection tunnel section 14 are radiated. Radiation is therefore also prevented from leaving the inspection apparatus from a container exit side. The controller (see reference numeral 36 in FIG. 2) may be programmed so that the line scanner 32 and the CT scanner subsystem 34 are switched off when both the third curtain 56C and the fourth curtain 56D are at least partially open. Sensors may for example be provided which detect the positioning of the curtains 56C and 56D and which forward the detected information to the controller.

Next, as illustrated in FIG. 3i, the fourth curtain 56D is raised and the first container 60 is moved out of the unloading tunnel section 16 through the second end of the unloading tunnel section 16. The third curtain 56C remains in a down position, thus preventing radiation within the inspection tunnel section 14 from reaching the unloading tunnel section 16.

For a complete discussion, FIG. 3j illustrates the inspection apparatus after the fourth curtain 56D is lowered. The second container 62 may at this stage be located within the inspection tunnel section 14. FIG. 3j is thus similar to FIG. 3f. The above described steps may then be repeated for a third and following containers.

It should be evident from the aforegoing description of FIG. 3a to FIG. 3j that one advantage of the inspection apparatus is that the confines of the inspection tunnel section 14 can be continuously radiated, i.e. without having to turn off a radiation source accompanied by delay in inspection of containers.

Continuous Scanning

Referring briefly to FIG. 3e to FIG. 3g, the container 60 is scanned while moving into (FIG. 3e), while located within (FIG. 3f) and while moving out of (FIG. 3g) the inspection tunnel section 14. The manner in which the container 60 is scanned and certain related features are now described with reference to FIG. 4a to FIG. 4c which correspond to FIG. 3e to FIG. 3g, respectively.

In the following description of FIG. 3e to FIG. 3g, detailed aspects relating to software used in the inspection apparatus, are not described in detail since the patents of Peschmann, referenced previously, teaches the general principles and techniques whereby objects of interest, such as explosives hidden in a closed container, are nonintrusively detected utilizing certain existing x-ray technique-based nonintrusive inspection apparatus. The Peschmann patents teach many details of the general and specific implementation of the present invention wherein the x-ray line scanner may be used to form a convention x-ray projection image, and in which software programs residing in the memory of a computer may be used to analyze the x-ray line scanner images, and to identify locations within a container being scanned that may deserve more detailed x-ray technique-based nonintrusive inspection. Peschmann teaches further that upon identifying such locations in the container, the container may be positioned with respect to the imaging plane of a CT scanner subsystem, such that a sequence of cross-sectional images of the container may be acquired at the locations so specified. Peschman further teaches that additional software programs that may reside in the memory of a computer may be used to analyze the cross-sectional images formed by the CT scanner subsystem, and that additional software programs that may reside in the memory of a computer may analyze all of the data available from both the x-ray line scanner subsystem and the CT scanner subsystem to render decision as to the likely presence of an object of interest such as an explosive hidden in the container.

As previously mentioned, the x-ray line scanner subsystem and the CT scanner subsystem (reference numerals 32 and 34 in FIG. 2) are located relatively close to one another. In addition to such a set of general and specific details of implementation provided by the Peschman patents, the present invention now provides particular scanning methods that enable the inspection apparatus 8 to be designed more compactly by permitting imaging planes of the x-ray line scanner subsystem and the CT scanner subsystem to be located closer to one another than would be otherwise possible, while still being capable of achieving a high rate of inspection of containers. What should be understood, however, is that the controller (reference numeral 36 in FIG. 2) is programmed to carry out the steps illustrated in FIG. 4a(i) to FIG. 4c(ii).

Figure 4:
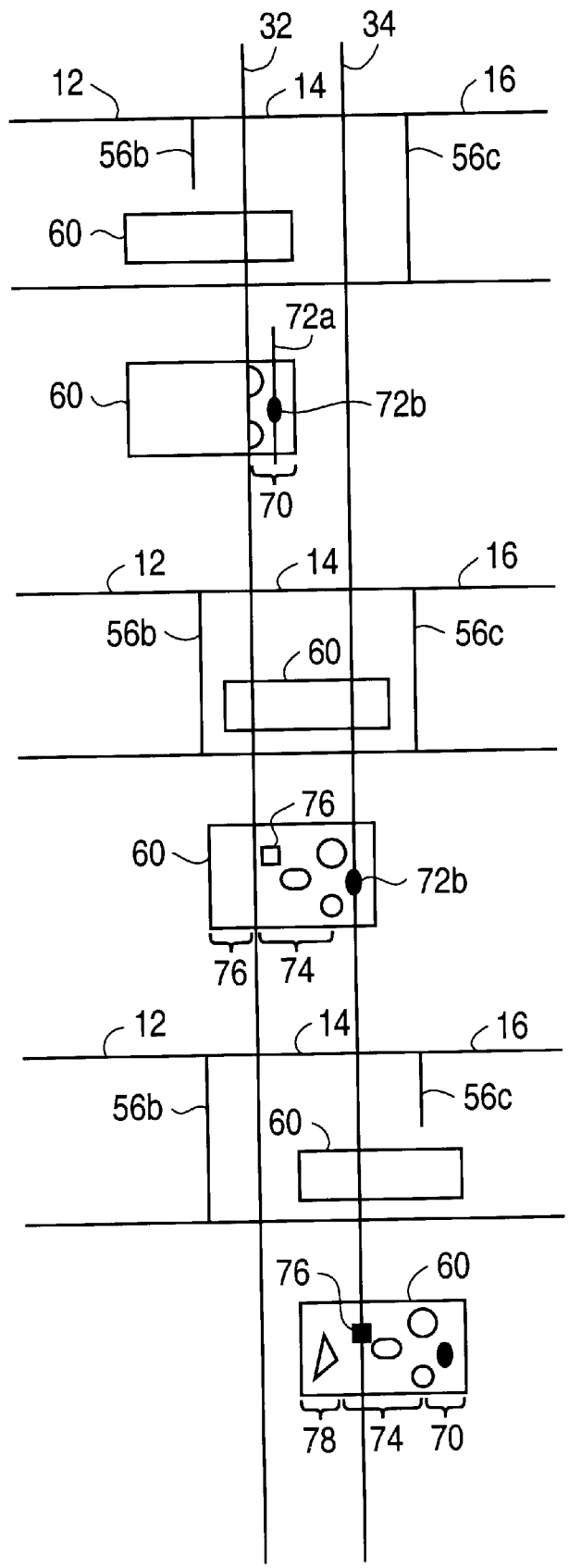
FIG. 4a(i) is a view similar to FIG. 3e, further illustrating the positioning of the container relative to an imaging plane of an x-ray line scanner subsystem forming part of the inspection apparatus.
FIG. 4b(i) is a view similar to FIG. 3f, further illustrating the positioning of the container relative to the imaging plane of the x-ray line scanner subsystem and an imaging plane of a CT scanner subsystem forming part of the inspection apparatus when the CT scanner subsystem is used for scanning at a location of interest within the container that may correspond with an object of interest.
FIG. 4c(i) is a view similar to FIG. 3g, further illustrating the positioning of the container relative to the respective imaging planes of the x-ray line scanner subsystem and the CT scanner subsystem when the CT scanner subsystem is used for scanning another location of interest within the container.

Referring to FIG. 4a(i), the container 60 is illustrated as it passes from the loading tunnel section 12 into the inspection tunnel section 14. An imaging plane of the x-ray line scanner subsystem is represented by the line 32 and an imaging plane of the CT scanner subsystem is represented by the line 34. The imaging plane 32 of the x-ray line scanner subsystem may be spaced from the second curtain 56B by a distance which is less than the length of the container 60 so that the container 60 starts moving to the imaging plane 32 of the x-ray line scanner subsystem before being entirely located within the inspection tunnel section 14.

FIG. 4a(ii) is a view of the container 60, illustrating the container 60 after a first front portion 70 has been moved past the imaging plane 32 of the x-ray line scanning subsystem. Inspection software analyzing the image formed by the x-ray line scanning subsystem represents the first front portion 70 of the container 60, and may at this stage detect a location 72A within the first front portion 70 which may contain an object of interest 72B. Alternatively, the inspection software may determine, based on other rules, that the specific location 72A within the first front portion 70 of the container 60 requires further measurements by the CT scanner subsystem.

Acquisition of the x-ray line scanner image continues whenever the container progresses past the imaging plane 32 of the x-ray line scanner subsystem. This image acquisition does not necessarily require the container to move continuously, nor does it necessarily require the container to move at a constant speed or in a single direction.

Once the location 72A has been identified, the speed at which the container 60 moves may then be progressively reduced and the container 60 may be brought to a standstill, as illustrated in FIG. 4b(i) and FIG. 4b(ii), with the location of interest 72A located in the imaging plane 34 of the CT scanner subsystem. Movement of the container 60 and acquisition of the x-ray line scanner image is thus position dependent as opposed to, for example, time dependent. Once the container 60 has stopped, the CT scanner subsystem 34 may scan the location of interest 72A.

In the time between identifying the location of interest 72A and the time at which the container is stopped with the location of interest 72A within the imaging plane 34 of the CT scanner subsystem, the x-ray line scanner subsystem may scan a second front portion 74 for of the container 60. A second object of interest 76 may be detected by the x-ray line scanner subsystem 32. Note that the imaging plane 32 of the x-ray line scanner subsystem and imaging plane 34 of the CT scanner subsystem may be spaced from one another by a distance which is less than the overall length of the container 60 so that the container 60 passes through the imaging plane 34 of the CT scanner subsystem before a rear portion 78 of the container 60 passes through the x-ray line scanning plane 32.

The container 60 may then be advanced until the second object of interest 76 is located in the imaging plane 34 of the CT scanner subsystem, as illustrated in FIG. 4c(i) and FIG. 4c(ii). The imaging plane 34 of the CT scanner subsystem may be spaced from the third curtain 56C by a distance which is less than the overall length of the container 60 so that the container 60 is already partially located within the unloading tunnel section 16. In the meantime, the x-ray line scanner subsystem 32 may scan the rear portion 78 of the container 60.

Note that the container 60 may therefore be moved through the inspection tunnel section 14 without altering the direction of movement of the container 60 relative to the x-ray line scanner subsystem 32 and the CT scanner subsystem 34.

Because the first curtain 56B, the imaging plane 32 of the x-ray line scanner subsystem, the imaging plane 34 of the CT scanner subsystem, and the third curtain 56C are spaced from one another by relatively small distances, the overall length of the inspection tunnel section 14 is relatively short. In one example the imaging plane 32 of the x-ray scanner subsystem is spaced from the first curtain 56B by a distance of about 34 centimeters, the imaging plane 34 of the CT scanner subsystem is spaced from the imaging plane 32 of the x-ray line scanner subsystem by a distance of about 87 centimeters, the third curtain 56C is spaced from imaging plane 34 of the CT scanner subsystem by a distance of about 65 centimeters, and the overall length of the inspection tunnel section 14 is therefore about 186 centimeters.

Structural Integrity

Figure 5:
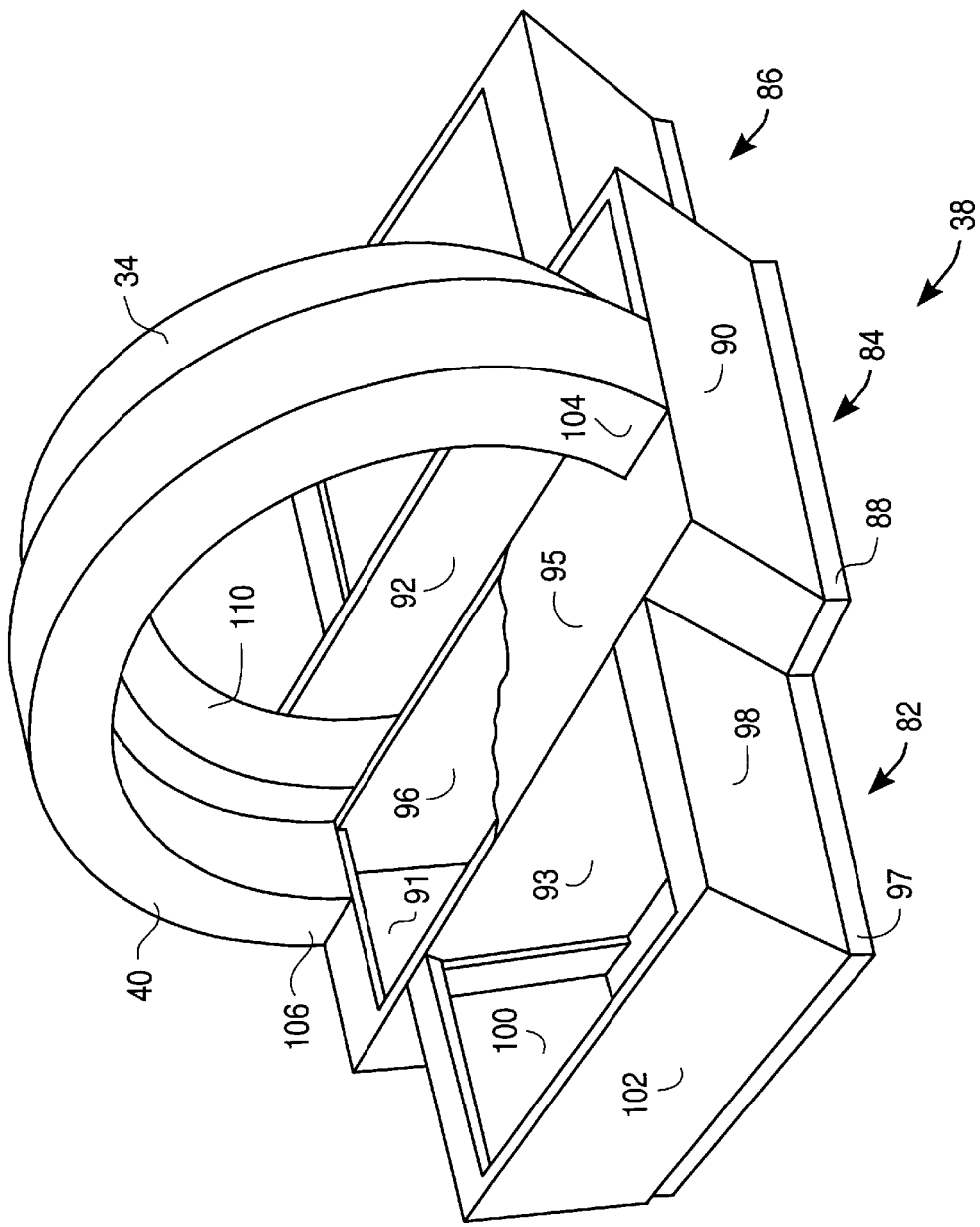
FIG. 5 is a perspective view of a support frame forming part of the inspection apparatus and the CT scanner subsystem.

FIG. 5 is a perspective view illustrating only the support frame 10 and the CT scanner subsystem 34. The base frame 38 is of monocoque design. Monocoque designs are frequently used, for example, in the design of the hulls of ships and in the design of the bodies of aircraft. In the present example, the base frame 38 generally has the shape of the hull of a ship in that the base frame 38 generally has a channel shape. Other components also form part of the base frame 38 which are similar to a bulkhead of a ship.

More specifically, the base frame 38 includes a first monocoque section 82, a second monocoque section 84, and a third monocoque section 86. It should be understood that the first monocoque section 82 is located in the region of the loading tunnel section, the second monocoque section 84 is located in the region of the inspection tunnel section, and the third monocoque section 86 is located in the region of the unloading tunnel section. (See reference numerals 12, 14 and 16 in FIG. 2).

The second monocoque section 84 has a base plate 88, first and second side walls 90 and 91 respectively, and first and second end walls 92 and 93 respectively. The side walls 90 and 91 are secured to the base plate 88 and extend upwardly from the base plate 88 and away from one another so that the base plate 88 and the first and second side walls 90 and 91 jointly define a channel shape which is wider at the top than at the bottom, similar to the hull of a ship when viewed in cross section. The end walls 92 and 93 are secured at spaced locations within the channel shape defined by the base plate 88 and the side walls 90 and 91, with edges of the end walls 92 and 93 secured to the base plate 88 and the side walls 90 and 91. Each end wall 93 or 94 is similar to a bulkhead of a ship. The channel shape of the second monocoque section 84 is extremely resistant to bending, and the channel shape together with the end walls 93 and 94 also provide torsional resistance to the second monocoque section 84.

Further components may be provided which give added support to the base frame 38. For example, a horizontal deck 95 may be secured to upper edges of the side walls 90 and 91 and the end wall 93, between the end wall 93 and the CT scanner subsystem 34. An additional vertical component 96 may be located on a side of the deck opposing the end wall 93 and have an upper edge secured to the deck, side edges secured to the side walls 90 and 91, and a bottom edge secured to the base plate 88. The deck and the additional vertical component are preferably located in the region of the arch 40 to provide additional rigidity to the base frame 38 in that region.

The first and third monocoque section 82 and 86 are similar to one another in design. Only the first monocoque section 82 is further described. It should however be understood that the description of the first monocoque section 82 that follows may also hold true for the third monocoque section 86.

The first monocoque section 82 has a base plate 97, first and second side walls 98 and 100, and an end wall 102. The side walls 98 and 100 are secured to the base plate 97 and extend upwardly from the base plate 97 and away from one another so that the base plate 97 and the first and second side walls 98 and 100 jointly define a channel shape which is wider at the top and at the bottom. The base plate 97 and the side walls 98 and 100 are positioned against the side walls 90 and 91 of the second monocoque section 84 and secured thereto. The end wall 102 is secured within the channel shape defined by the base plate 97 and the side walls 98 and 100 and on a side thereof opposing the end wall 93 of the second monocoque section 84. The channel shape of the first monocoque section 82 provides the first monocoque section 82 with resistance to bending and the end walls 93 and 102, together with the channel shape, provide torsional resistance to the first monocoque section 82.

The arch 40 has opposing ends 104 and 106 which are secured to the side walls 90 and 91, respectively, of the second monocoque section 84. A bearing (not shown) is located within the arch 40 and the CT scanner subsystem 34 is mounted to a rotational portion of the bearing.

In use, the CT scanner subsystem 34 may rotate at a rate of about 120 revolutions per minute. Furthermore, it may be required that the CT scanner subsystem 34 be relatively large. One reason for the size requirement of the CT scanner subsystem 34 is so that larger containers may pass through the CT scanner subsystem 34. The CT scanner subsystem 34 may, for example define an opening 110 which is about 113 centimeters in diameter.

Another reason for the size requirement of the CT scanner subsystem 34 deals with the compatibility of the inspection apparatus with conveyor belts found within airports. Airport conveyor belts are typically about one meter wide. If the conveyor belts used within the inspection apparatus are less than one meter wide, additional channeling devices may have to be provided to reorient and channel containers from the airport conveyor belts to the conveyor belt of the loading tunnel section. (See reference numerals 50 and 12 in FIG. 2). For example, containers may be oriented on the airport conveyor belts so as to be oriented such that their longest the dimension lies transverse to the direction of motion of the conveyor belts. With smaller aperture apparatus, channeling devices may then have to be located between the airport conveyor belts and the inspection apparatus to reorient the containers so that their longest dimensions line up in a direction which is more or less parallel to the direction of motion of the conveyor belts so that the containers fit into the inspection apparatus and onto the conveyor belts used in the inspection apparatus. Such channeling devices may add to the overall length of the inspection apparatus and are preferably avoided. The conveyor belts used within the inspection apparatus 8 are therefore preferably about one meter wide, which means that a one-meter wide conveyor belt should be able to pass through the CT scanner subsystem 34.

However, the relatively large diameter of the CT scanner, together with its high rotational rate, may cause very strong forces to be applied to the base frame 38. The forces may occur inadvertently due to an unbalanced operating condition arising from any cause. Furthermore, the relatively large diameter of the CT scanner subsystem together with a requirement to accelerate quickly to a high rate of revolution, or decelerate quickly, may cause very strong torsional forces on the base frame 38 when rotation of the CT scanner subsystem 34 is started or stopped. It should be evident from the aforegoing description that the base frame 38 is designed to deal with the high forces which may tend to bend or induce vibration in the base frame 38 when the CT scanner subsystem 34 is in an unbalanced condition, for example, and resist the relatively high torsional forces which act on the base frame 38 when rotation of the CT scanner subsystem 34 is started or stopped.

It should be evident from the aforegoing description that the design of the base frame 38 is related to the width of the conveyor belts that are used within the inspection apparatus and that the conveyor belts may be sufficiently wide so that reorienting of containers may be avoided. The containers may thus enter the inspection apparatus while being oriented with their longest dimensions transverse to the direction of motion of the conveyor belts. Because the containers may be oriented in such a manner, a container may therefore be oriented so that the width of the container may be located in a direction approximately parallel to the direction of motion of the conveyor belts, thus potentially permitting container inspection to be completed with a smaller number of CT scanning slices than would be required to complete an equally effective inspection were the container to be oriented differently.

Radiation Containment

FIG. 6 illustrates a portion of the arch 40, the inspection tunnel section 14, the x-ray line scanner subsystem 32, and the CT scanner subsystem 34. The inspection tunnel section 14 includes a first tunnel portion 120, a second tunnel portion 122, and a third tunnel portion 124 which are all nonrotatably mounted to the base frame. (See reference numeral 38 in FIG. 2).

The first tunnel portion 120 is located on a side of the x-ray line scanner subsystem 32 opposing the CT scanner subsystem 34 and has a first end 126 which is also the first end 42 of the inspection tunnel section 14, and a second end 128, opposing the first end 126, against the x-ray line scanner subsystem 32.

The second tunnel portion 122 is located between the x-ray line scanner subsystem 32 and the CT scanner subsystem 34 and has a first end 130 against the x-ray line scanner subsystem 32, and a second end 132, opposing the first end 130, at the CT scanner subsystem 34.

The third tunnel portion 124 is located on a side of the CT scanner subsystem 34 opposing the x-ray line scanner subsystem 32 and has a first end 134 at the CT scanner subsystem 34 and a second end 136, opposing the first end 134, which is also the second end 44 of the inspection tunnel section 14.

The x-ray line scanner subsystem 32 is nonrotatably mounted to the arch 40 and includes a partial gantry enclosure 138 and a radiation tube 140. Other features of the x-ray line scanner subsystem 32 are similar to those of the CT scanner subsystem 34 and the CT scanner subsystem 34 is described in more detail hereinbelow.

The arch 40 is located around the second tunnel portion 122 and defines a bearing housing 142 around the second tunnel portion 122. The bearing housing 142 is open towards the CT scanner subsystem 34. A bearing 144 is located within the bearing housing 142. The CT scanner subsystem 34 includes a gantry enclosure 148, an x-ray tube 150 which is secured to the gantry enclosure 148, and a ring 152 which is secured to the gantry enclosure 148. The ring 152 extends into the bearing housing 142 and is located on a rotating portion of the bearing 144, thus mounting the CT scanner subsystem 34 rotatably to the arch 40. The CT scanner subsystem 34 rotates around the inspection tunnel section 14.

Figure 7:
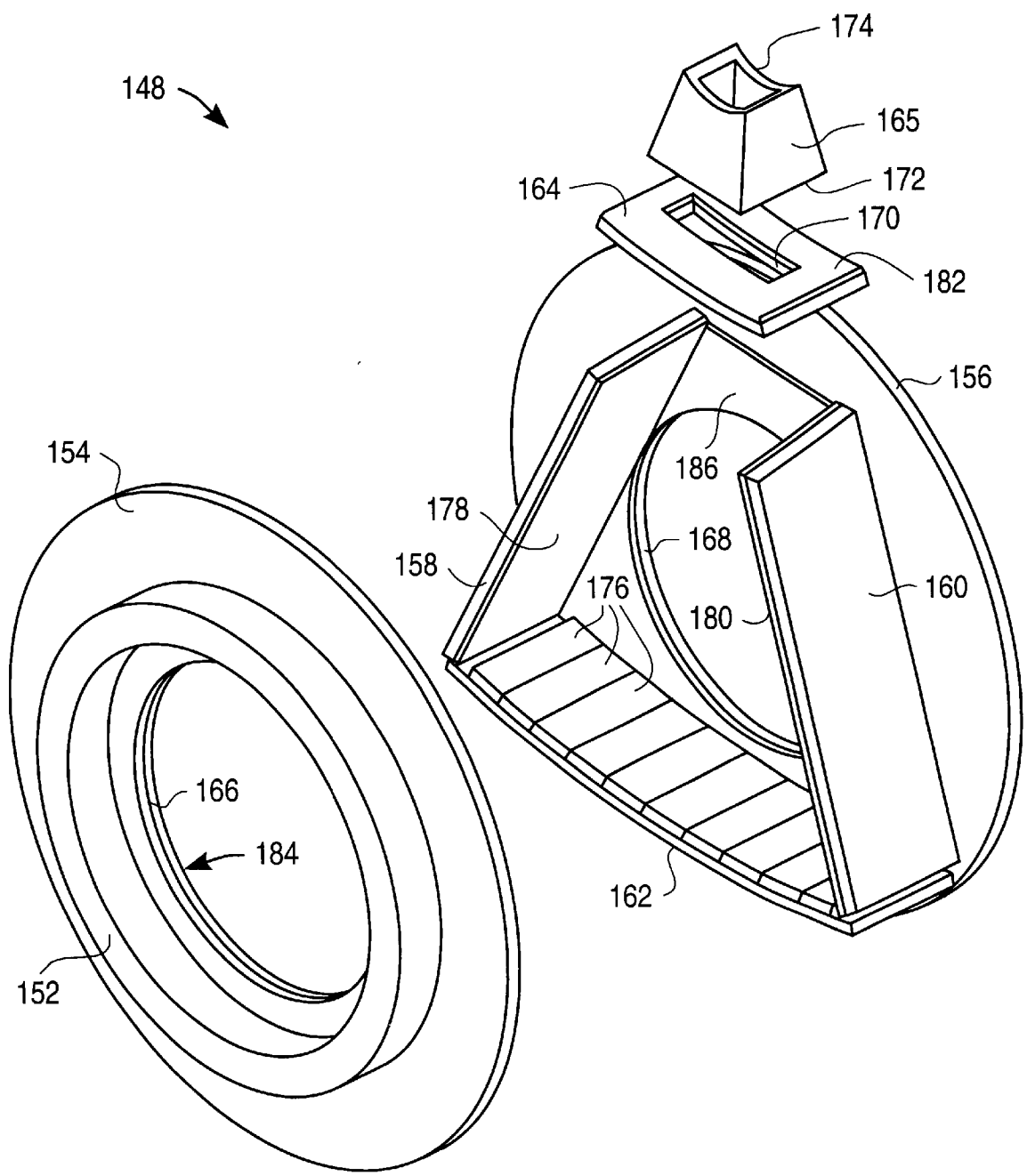
FIG. 7 is a perspective view illustrating in exploded form a gantry enclosure forming part of the CT scanner subsystem.

FIG. 7 illustrates the gantry enclosure 148 and the ring 152 of the CT scanner subsystem 34 in more detail.

The gantry enclosure 148 includes first and second spaced gantry plates, 154 and 156 respectively, first, second, and third spacers 158, 160, and 162 respectively, a collimator face 164, and a hollow, substantially frustum pyramidal collimator component 165.

The first gantry plate 154 has a gantry aperture 166 formed therein and the second gantry plate 156 also has a gantry aperture 168 formed therein. The ring 152 is mounted to the first gantry plate 154 around the gantry aperture 166 in the first gantry plate 154.

The collimator face 164 is curved and a hole 170 is formed in the collimator face 164. The collimator component 165 has a base 172 which is slightly larger than the hole 170 in the collimator face 164. The collimator component 165 also has an apex 174 which is smaller than the base 172 and which is formed so as to fit snugly against the x-ray tube. (See reference numeral 150 in FIG. 6). When the base 172 of the collimator component 165 is positioned over the hole 170 and the collimator component 165 is mounted to the collimator face 164, the hole 170 may only be accessed through the apex 174 of the collimator component 165.

The first and second gantry plates 154 and 156 are secured to the spacers 158, 160, and 162, with the spacers being located between the gantry plates and around the gantry apertures 166 and 168. The first and second spacers 158 and 160 may be made of a material such as aluminum. The third spacer 162 has a curved shape and may also be made of a material such as aluminum.

The collimator face 164 may also be made of a material such as aluminum and is shorter than the third spacer 162.

The spacers 158, 160, and 162 and the collimator face 164 are positioned in a trapezium-like shape with the third spacer 162 and the collimator face 164 respectively forming a long side and a short side of the trapezium and the first and second spacers 158 and 160 connecting edges of the third spacer 162 and the collimator face 164 so that the first and second spacers 158 and 160 are spaced closer to one another at the collimator face 164 and further from one another at the third spacer 162.

The gantry enclosure 148 is so partially defined by the first and second gantry plates 154 and 156, the spacers 158, 160, and 162, and the collimator face 164. The only areas of the gantry enclosure 148 which are open are due to the gantry apertures 166 and 168 in the first and second gantry plates 154 and 156 respectively, and due to the hole 170 in the collimator face 164.

The gantry enclosure 148 includes lead lining which prevents radiation from escaping from the gantry enclosure 148. Lead tiles 176 are mounted to the third spacer 162 within the gantry enclosure 148. Lead plates 178, 180 are also secured to the first spacer 158 and the second spacer 160, respectively, within the gantry enclosure 148, and a lead plate 182 is secured to the collimator face externally of the gantry enclosure 148. A lead liner 184 is also secured to the first gantry plate 154 on a side thereof facing into the gantry enclosure 148, and another lead liner 186 is secured to the second gantry plate 156 on a side thereof facing into the gantry enclosure 148. The lead liners 184 and 186 conform to the internal dimensions of the gantry enclosure 148. In addition, the collimator component 165 is made of the lead. It can thus be seen that the entire gantry enclosure 148 is lead lined and thus resistant to transmission of x-ray radiation. The only areas through which x-ray radiation may pass into or out of the gantry enclosure 148 are the apex 174 of the collimator component 165 and the gantry apertures 166 and 168 in the first and second gantry plates 154 and 156, respectively.

Referring again to FIG. 6, the x-ray tube 150 fits snugly on the apex 174 of the collimator component 165. A lead lining 188 covers all inner surfaces of the x-ray tube 150, except an area of the x-ray tube 150 directly over the apex 174 of the collimator component 165. The entire area including the x-ray tube 150 and the collimator component 174 is thus enclosed by lead. It should now the evident that, when the x-ray tube 150 is activated, x-rays are transmitted from the x-ray tube 150 through the collimator component 165 into the confines of the gantry enclosure 148. X-ray radiation may only escape through the gantry apertures 166 and 168 in the first and second gantry plates 154 and 156 respectively.

Detector arrays 190 are located within the gantry enclosure 148 on a side of the gantry enclosure 148 opposing the x-ray tube 150. The detector arrays 190 may for example be mounted to the lead tiles 176. Conductors 192 are connected to the detector arrays 190 and extend through the lead tiles 176 and the third spacer 162 so as to provide an electrical connection between the detector arrays 190 and externally of the gantry enclosure 148.

The x-ray line scanner subsystem 32 may have a similar construction to the CT scanner subsystem 34 and is lead lined in a manner similar to the CT scanner subsystem 34.

Lead linings 196, 198 and 200 are also formed on the internal dimensions of the first, second and third tunnel portions 120, 122 and 124, respectively. Lead linings 196 and 198 of the first and second tunnel portions 120 and 122 are sufficiently close and overlapping the lead linings of the x-ray line scanner subsystem 32 so that interfaces between the x-ray line scanner subsystem 32 and the first and second tunnel portions 120 and 122 are, in a radiation sense, substantially sealed.

The second end 132 of the (stationary) second tunnel portion 122 extends into the gantry aperture 166 in the first gantry plate 154 of the (rotatable) CT scanner subsystem 34. The lead lining 198 on the second tunnel portion 122 is located relatively close and overlapping the lead liner 184 on the first gantry plate 154 and is separated therefrom only by a gap which is necessary to allow for rotation of the CT scanner subsystem 34 relative to the second tunnel portion 122. And interface between the second tunnel portion 122 and the CT scanner subsystem 34 is thus, in a radiation sense, substantially sealed.

Similarly, the first end 134 of the third tunnel portion 124 extends into the gantry aperture 168 of the second gantry plate 156, and the lead lining 200 is located relatively close to the lead liner 186 so that an interface between the third tunnel portion 124 and the second gantry plate 156 is, in a radiation sense, substantially sealed.

Referring again to FIG. 2, the internal dimensions of the loading and unloading tunnel sections 12 and 16 are also lead lined. Each curtain 56 is made of a number of layers which are located over one another, including a number of layers containing significant amounts of lead.

It should be evident that the entire inspection apparatus 8 is self shielded against in the sense that it effectively attenuates leaking of radiation therefrom and that no extraneous radiation resistant shielding members have to be provided for purposes of radiation containment. Because no extraneous radiation shielding members have to be provided, much less lead lining is required—see for example how the x-ray tube 150 is lead lined with the minimal amount of lead.

The lead on the CT scanner subsystem 34 does make it somewhat heavier, with corresponding consequences as far as stresses and strains on the base frame are concerned. (See reference numerals 38 in FIG. 5). The base frame is, as described with reference to FIG. 5, however designed to deal with relatively large forces.

Although self shielding has been specifically described with reference to an x-ray technique-based nonintrusive inspection apparatus for inspection of containers, the principles of self shielding may also find application in related technologies such as CT scanning of people and other patients. A self shielded CT scanner may be located within a room and be used for inspecting and diagnosing of a patient. Since the CT scanner is self shielded, the patient may be inspected, utilizing the CT scanner, while people are located around the CT scanner within the same room. Furthermore, such self-shielded apparatus would obviate the need and cost of providing special rooms with walls, floors, and ceilings which are capable of providing such radiation shielding.

Driving Arrangement

Figure 8:
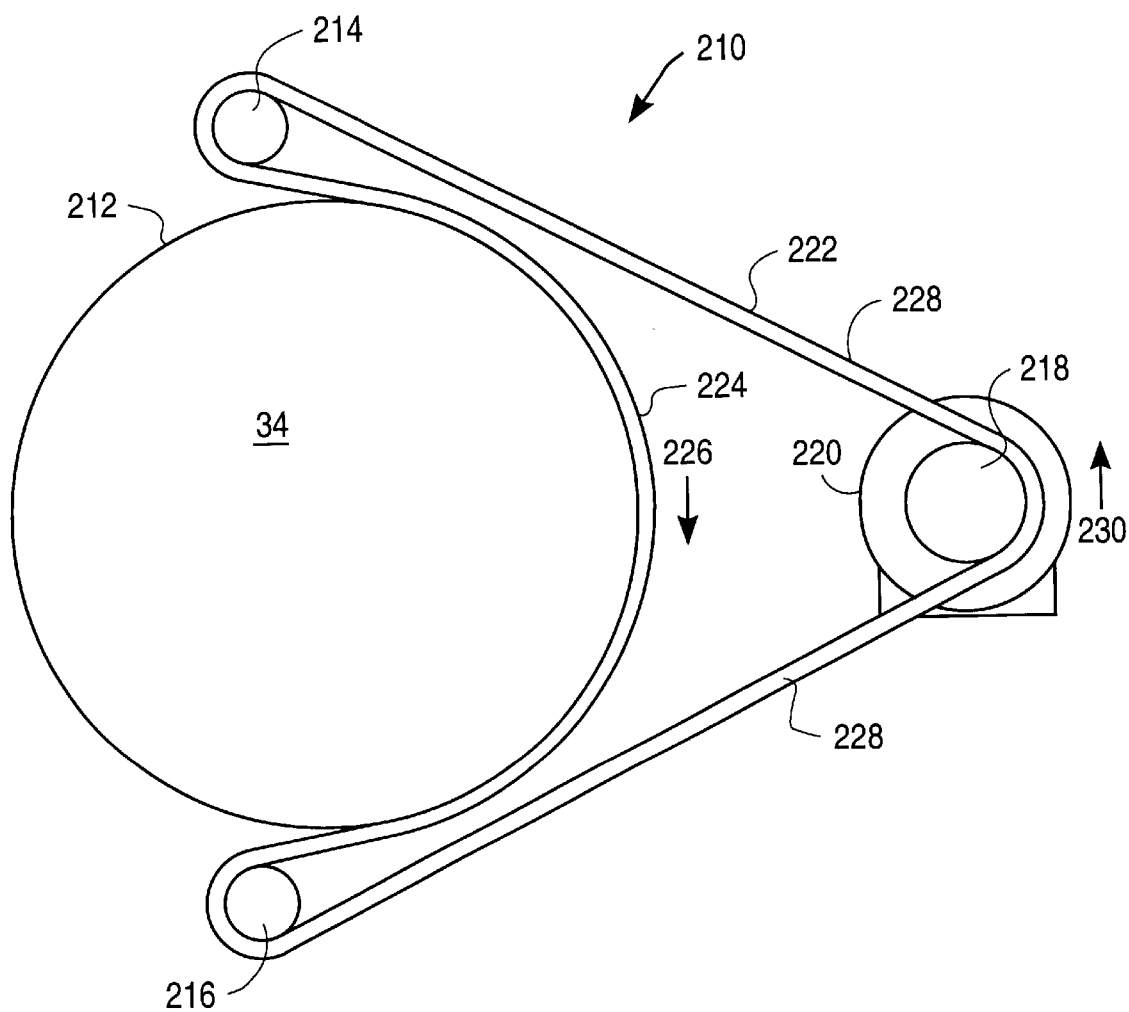
FIG. 8 is an end view illustrating a driving arrangement which is used for rotating the CT scanner subsystem.

FIG. 8 illustrates in end view the CT scanner subsystem 34 and a driving arrangement 210 forming part of the x-ray technique-based nonintrusive inspection apparatus and which is used for rotating the CT scanner subsystem 34.

It should be evident from the aforegoing description that the CT scanner subsystem 34 is rotatably mounted to the arch of the support frame. (See for example reference numerals 10 and 40 in FIG. 2 and FIG. 5). The CT scanner subsystem 34 has a circular outer surface 212 which may, for example, be on a ring which may be secured to the gantry enclosure. (See reference numeral 148 in FIG. 6).

The driving arrangement 210 includes first, second and third pulleys 214, 216 and 218, respectively, an electric motor 220, and a flexible member 222, such as a flexible belt or a chain, forming a closed loop. The pulleys 214, 216 and 218 are located at various locations around the C. T. scanner subsystem 34. The first and second pulleys 214 and 216 are rotatably mounted to the support frame. (See reference numeral 10 in FIG. 2). The electric motor 220 is also mounted to the support frame and the third pulley 218 is directly coupled and mounted to a shaft of the electric motor 220 so as to be rotated by the electric motor 220 when the electric motor 220 is operated.

The flexible member 222 encircles and runs over the first, second and third pulleys 214, 216 and 218, respectively. When stationary, or at any given moment while moving over the pulleys 214, 216, and 218, the flexible member 222 has a first section 224 running from the first pulley 214 to the second pulley 216 in a first direction 226 around and over the circular outer surface 212. The flexible member 222 also has a second section 228 returning from the second pulley 216 over the third pulley 218 back to the first pulley 214 in a second direction 230, which is opposite to the first direction 226, around the circular outer surface 212.

In use, when the third pulley 218 is rotated by the electric motor 220, the flexible member 222 progresses over the pulleys 214, 216 and 218, for example in an anti-clockwise direction. Because of progression of the flexible member 222, the CT scanner subsystem 34 is rotated in a clockwise direction.

It can thus the seen that a complete revolution of the flexible member 222 does not entirely encircle the CT scanner subsystem 34. Because of the positioning of the flexible member 222, it may be engaged with the circular outer surface 212 without having to be positioned so that it surrounds the CT scanner subsystem 34, the inspection tunnel section, or the inspection conveyor apparatus. The flexible member 222 may thus be installed without obstruction from the CT scanner subsystem 34 itself or obstruction from the inspection tunnel section of the inspection conveyor apparatus which are mounted to the base portion in the vicinity of the CT scanner subsystem 34. (See reference numerals 14, 20 and 38 in FIG. 1). Maintenance due to failure of the flexible member 222 is thus greatly simplified.

In other embodiments more pulleys may be used serving various purposes such as tensioning of the flexible member 222, or the flexible member 222 may be driven by a separate device.

Shielding Arrangements

Figure 9:
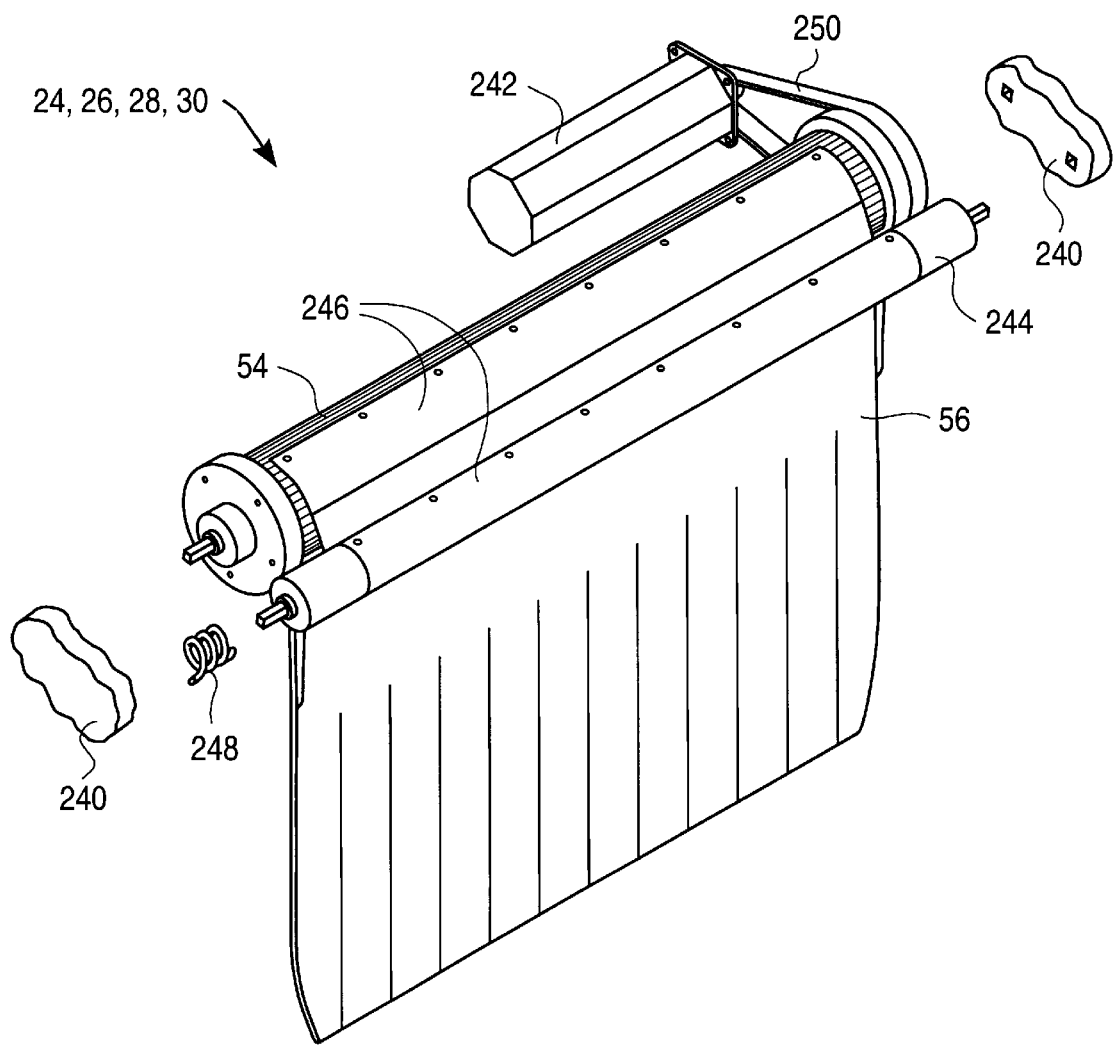
FIG. 9 is a perspective view of a shielding arrangement which is incorporated into a shielding apparatus forming part of the x-ray technique-based nonintrusive inspection apparatus.

FIG. 9 illustrates one of the shielding arrangements 24, 26, 28 or 30 of FIG. 2 in more detail. The shielding arrangement 24, 26, 28 or 30 forms part of a larger shielding apparatus which includes support structures 240 which are mounted to the base frame and which form part of the support frame of the x-ray technique-based nonintrusive inspection apparatus of the invention. (See reference numerals 8, 10 and 38 in FIG. 2).

Each shielding arrangement 24, 26, 28 or 30 includes, in addition to the curtain roller 54 and the radiation resistant curtain 56, also an electric motor 242, a tensioning roller 244, a flexible sheet 246, and a torsion spring 248.

The curtain roller 54 is rotatably mounted between the support structures 240, and the curtain 56, as previously mentioned, is secured to the curtain roller 54 so as to be rolled onto or from the curtain roller 54 upon rotation of the curtain roller 54.

The electric motor 242 is also secured to one of the support structures 240. A driving belt 250 couples the electric motor 242 to the curtain roller 54 so that the curtain roller 54 is rotated upon operation of the electric motor 242. The rotational positioning of the curtain roller 54, and therefore also the height of the curtain 56, is also determined by the electric motor 242.

The sheet 246 has one portion attached to the curtain roller 54 and a second portion attached to the tensioning roller 244. The sheet 246 is rolled onto the tensioning roller 244.

The tensioning roller 244 is also rotatably mounted between the support structures 240. The torsion spring 248 is located between one of the support structures 240 and that tensioning roller 244. The torsion spring 248 is under torsion, i.e. the torsion spring 248 is torsionally biased, thus tending to rotate the tensioning roller 244. The tensioning roller 244 is, however, prevented from rotating because the tensioning roller 244 is connected by the sheet 246 to the curtain roller 54 and the rotational position of the curtain roller 54 is determined by the electric motor 242. It should thus be evident that the sheet 246 is under tension between the curtain roller 54 and the tensioning roller 244 because of the tendency of the tensioning roller 244 to rotate and the predetermined rotational positioning of the curtain roller 54.

Figure 10:
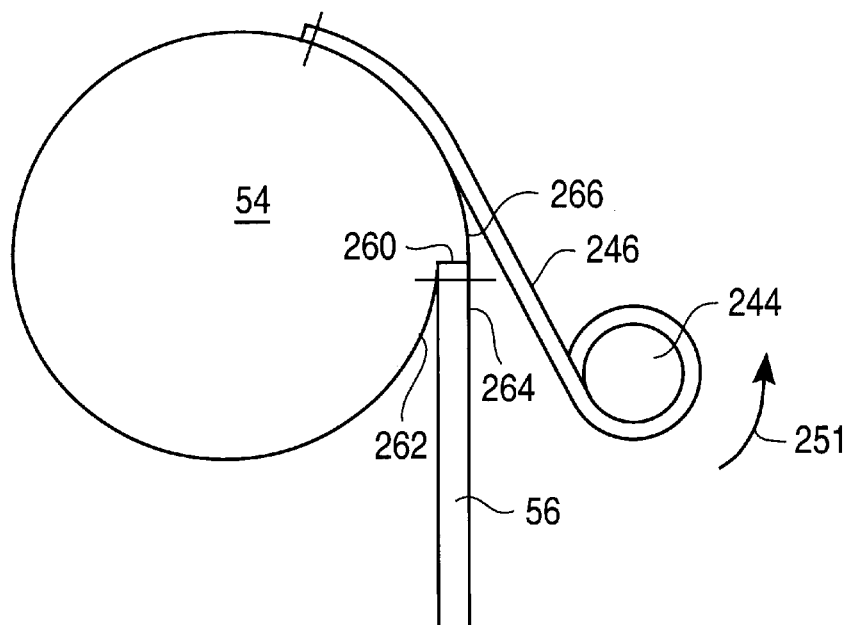
FIG. 10 is an end view of the shielding arrangement of FIG. 9 before a radiation resistant curtain thereof is rolled onto a curtain roller thereof.

FIG. 10 illustrates the arrangement of FIG. 9 in end view. The curtain 56 hangs from one side of the curtain roller 54. The tensioning roller 244 is located on the same side of the curtain roller 54 as the side of the curtain roller 54 from which the curtain 56 hangs, with the curtain 56 being located between the curtain roller 54 and the tensioning roller 244.

The sheet 246 passes from under the tensioning roller 244 over and onto the curtain roller 54. The sheet 246 therefore extends clockwise around the tensioning roller 244 and anti-clockwise around a portion of the curtain roller 54.

The tensioning roller 244 has a tendency to rotate in an anti-clockwise direction 251. Because of the tendency of the tensioning roller 244 to rotate in an anti-clockwise direction, and the connection between the tensioning roller 244 and the curtain roller 54, the curtain roller has a tendency to rotate in a clockwise direction. Rotation of the curtain roller 54 in an anti-clockwise direction results in rolling of the curtain 56 onto the curtain roller 54 and rotation of the curtain roller 54 in a clockwise direction results in rolling of the curtain 56 from the curtain roller 54. The tensioning roller 244 thus tends to roll the curtain 56 from the curtain roller 54.

The tensioning roller 244 and the sheet 246 ensure that the curtain 56 is rolled tightly and in a controlled manner onto the curtain roller 54. The tensioning roller 244 and the sheet 246 also ensure that the curtain 56 remains tightly on the curtain roller 54 when rotation of the curtain roller 54 in an anti-clockwise direction is decelerated. The tensioning roller 244 and the sheet 246 also ensure that the curtain 56 remains tightly on the curtain roller 54 when the curtain roller 54 is rotated in a clockwise direction.

Figure 11:
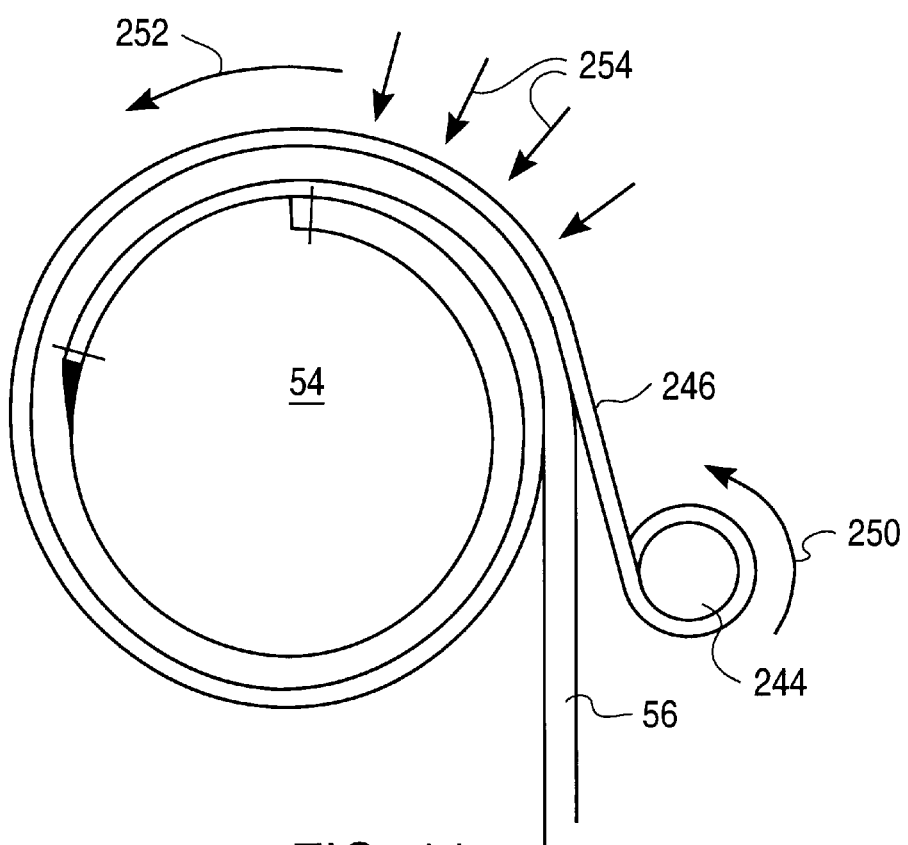
FIG. 11 is a view similar to FIG. 10 while the curtain is rolled onto the curtain roller, further illustrating the effect of a tensioning apparatus which controls rolling of the curtain onto the curtain roller.

For example, FIG. 11 illustrates the arrangement of FIG. 10 when the curtain 56 is rolled onto the curtain roller 54 by rotation of the curtain roller 54 in an anti-clockwise direction 252. The sheet 246 is rolled together with the curtain 56 onto the curtain roller 54 with the sheet 246 being located on an outer surface of the curtain 56. Due to the tension present in the sheet 246, the sheet 246 creates a force 254 on the curtain 56 which is radially inward towards the curtain roller 54. Because of the force 254, the curtain 56 is maintained in close contact with the curtain roller 54 and preceding layers of the curtain 56 when the curtain 56 is rolled onto the curtain roller 54.

When the curtain roller 54 is rotated in an anti-clockwise direction, the curtain 56 has momentum. When the curtain roller 54 is brought to a halt, after being rotated in an anti-clockwise direction, the momentum of the curtain 56 will tend to lift the curtain 56 from the curtain roller 54 or preceding layers of the curtain 56 on the curtain roller 54. The tendency of the curtain 56 to lift is, however, counteracted by the force 254.

When the curtain roller 54 is accelerated in a clockwise direction, lack of momentum of the curtain 56 will attend tend to cause the curtain 56 to lift, which tendency is again counteracted by the force 254.

By correctly positioning the tensioning roller 244, the trajectory of the curtain 56 when it rolls off the curtain roller 54 can also be controlled. The trajectory of the curtain 56 is preferably substantially vertically downwardly. Vertical downward movement of the curtain 56 is preferred because waves within the curtain 56 or whiplash-like oscillations of the curtain 56 can so be avoided and the curtain 56 can thus the brought to standstill much quicker.

Referring again to FIG. 10, it should also be noted that the curtain roller 54 has an outer surface which has a shape which is generally in the form of a spiral having a step 260. An end of the curtain 56 is secured to an inner portion 262 of the spiral with a edge of the curtain 56 adjacent the step 260. A surface 264 of the curtain 56 opposing the inner portion 262 is substantially in line with an outer portion 266 of the spiral.

When the curtain 56 is rolled onto the curtain roller 54, as illustrated in FIG. 10, up to the point where the curtain 56 starts rolling onto itself (the sheet 246 being located between layers of the curtain 56) a smooth transition is ensured. A smooth transition is important because waves within or whiplash-like oscillations of the curtain 56 may be avoided, and the power demanded of the drive motor is made more uniform in time. When the curtain 56 is rolled from the curtain roller 54 a smooth transition is also ensured which, in addition to the positioning of the tensioning roller 244, further prevents waves within or whiplash-like oscillations of the curtain 56.

It can thus be seen from the aforegoing description that the curtain 56 may be lowered and raised quickly and in a controlled manner both because of the tensioning roller 244 and the spiral shape of the curtain roller 54.

Detector Array Collimators

FIG. 12a(i) to FIG. 12c(ii) illustrate a method of making a collimator for a detector array of the CT scanner. (See reference numeral 34 in FIG. 2).

FIG. 12a(i) illustrates a die 310 which may be used for injection molding of such a body of a collimator. The die 310 includes a cup 312 and a shape defining element 314. The shape defining element 314 includes a substructure 316 and a plurality of fins 318 which are secured to the substructure 316. The fins 318 define a plurality of septa gaps 320 between them.

Referring to FIG. 12a(ii), the shape defining element 314 also includes delimiting portions 322 secured to the substructure 316 on opposing sides of the fins 318. The fins 318 are slightly longer than the delimiting portions 322.

FIG. 12b(i) illustrates the die 310 after the shape defining element 314 is inserted into the cup 312. The fins 318 extend all the way to a base of the cup 312.

In FIG. 12b(ii) it can be seen that L-shaped support structure gaps 324 are formed between opposing surfaces of the fins 318 and the delimiting portions 322, and between the delimiting portions 322 and the base of the cup 312. In another section through FIG. 12b(i), one will be able to see that the support structure gaps 324 and the septa gaps 320 are in communication with one another.

A material is injected into one of the support structure gaps 324 so that the material fills the support structure gaps 324 and the septa gaps 320. The material preferably comprises about 86 percent lead, 3 percent tin, and 11 percent antimony. The lead provides the material with x-ray radiation shielding capabilities, while the purpose of the alloy between the elements is to provide the material with the strength that lead, by itself, lacks.

The material is then allowed to set within the die 310 to form a body of a collimator which is then removed from the die 310 as will be further described hereinbelow with reference to FIG. 14. FIG. 12c(i) illustrates the body 330 of the collimator 332. The body 330 has a plurality of septa 334, formed in the septa gaps 320, which are located next to one another.

Referring to FIG. 12c(ii), it can be seen that support structures 336 are formed within the support structure gaps 324 and that the septa 334 are secured between and supported by the support structures 336. The support structures 336 include mounting portions 338 which are coplanar with one another, and walls 340 extending from the mounting portions 338 parallel to one another.

FIG. 13 is a perspective view of the collimator 332. Registration notches 341 are formed within sides of the mounting portions 338. The registration notches 341 allow for positioning and securing of a plurality of collimators such as the collimator 332 simply, reliably, and accurately in a modular fashion.

It can be seen from the aforegoing description that an effective and easy method is provided for forming the body 330 of the collimator 332.

More importantly, the body 330 has superior strength characteristics because of the materials used for forming the body and because of the manner in which the septa 334 are secured between the support structures 336. The collimator 332 may be located on a detector array of the CT scanner subsystem (see reference numeral 34 in FIG. 2) wherein the detector array rotates at a relatively large radius. The CT scanner subsystem may, in addition, rotate at a relatively high rate of revolution. The radius of rotation of the detector array, together with the relatively high rate of revolution of the CT scanner subsystem may cause large centrifugal forces to act on the collimator 332. The strength characteristics of the body 330 of the collimator 332 are thus important for dealing with the centrifugal forces.

Figure 14:
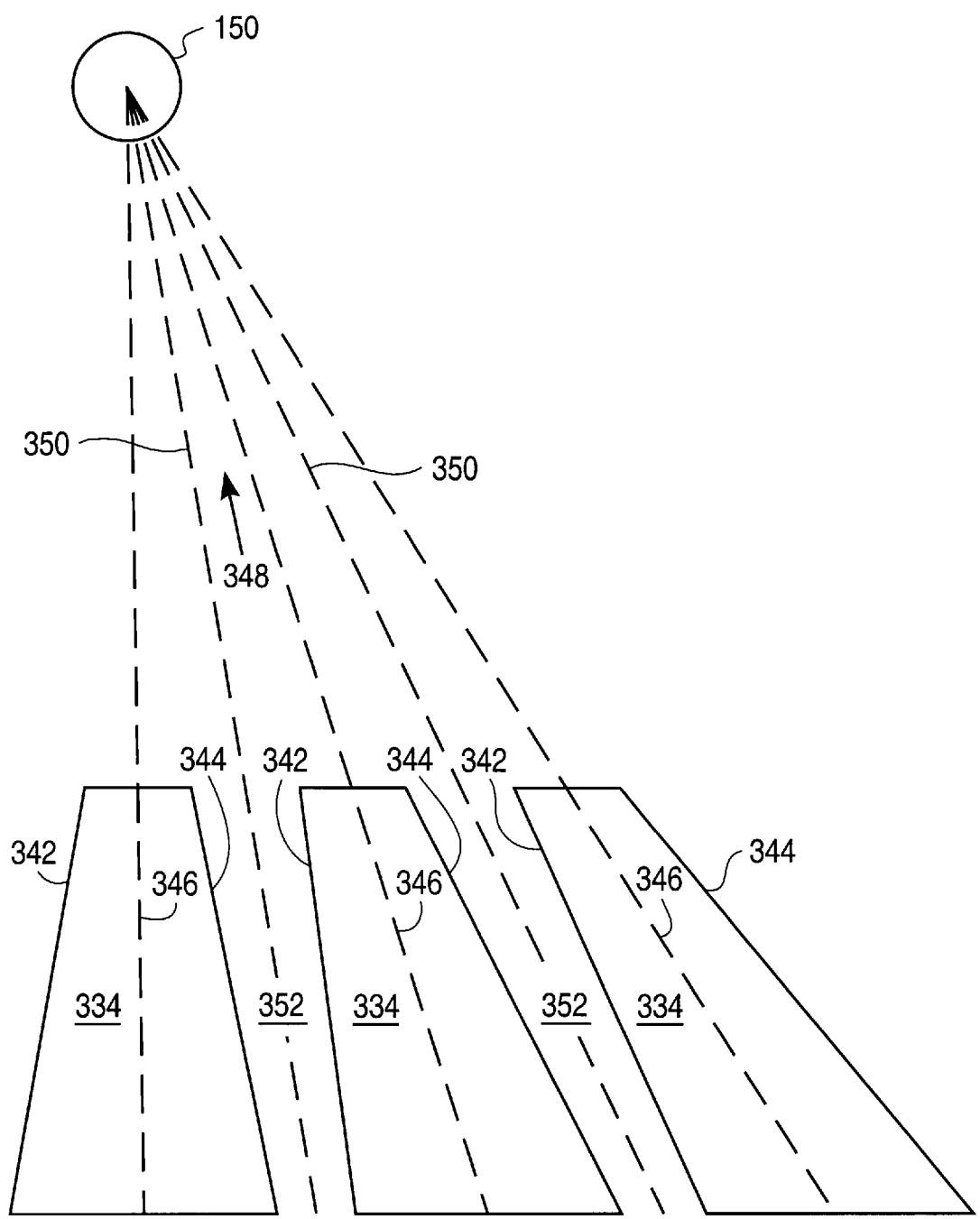
FIG. 14 is a cross-sectional view through septa of the detector array collimator of FIG. 13, illustrating in an exaggerated manner how the septa are formed.

FIG. 14 illustrates in much exaggerated detail an x-ray tube 150 which is used in the CT scanner subsystem (see reference numeral 150 in FIG. 6), and a view of the septa 334 when the collimator 332 of FIG. 12 and FIG. 13 is installed on a detector array (not shown).

Each septum 334 has first and second opposed surfaces 342 and 344, respectively, and a center line 346 between the surfaces 342 and 344. The center lines 346 converge towards one another in a direction 348 and meet at the x-ray tube 150. Because of the orientations of the center lines 346 relative to one another, x-rays 350 which are emitted by the x-ray tube 150 may pass through collimator apertures 352 between the septa 334 in a manner wherein the x-rays 350 are correctly collimated.

Surfaces 342 and 344 of two of the septa 334 which face one another do, however, not converge in the direction 348. As shown in the drawing, it may be possible that the opposing surfaces 342 and 344 of two of the septa 334 located next to one another may diverge from one another in the direction 348. The reason for the orientations of the opposing surfaces 342 and 344 relative to one another is so that the fins (see reference numeral 318 in FIG. 12b(i)), when the septa 334 are manufactured, may be removed. Each fin will therefore have opposing surfaces which are substantially parallel to one another or which taper towards one another in a direction from the substructure (see reference numeral 316 in FIG. 12a(i)) towards tips of the fins.

As mentioned, FIG. 14 is in greatly exaggerated detail. The angles between the center lines 346 of the septa 334 are, in practice, much smaller than indicated in FIG. 14. Removal of the fins is therefore not substantially hampered because of the angles of the center lines 346 relative to one another. In practice, for example, sixteen of the septa 334 may be provided, a lower tip of a first of the septa may be spaced from a lower tip of a sixteenth of the septa by a distance of about 50 millimeters, and an upper tip of the first septum may be spaced from an upper tip of the sixteenth septum by a distance of about 49 millimeters.

Container Jam Release

Figure 15:
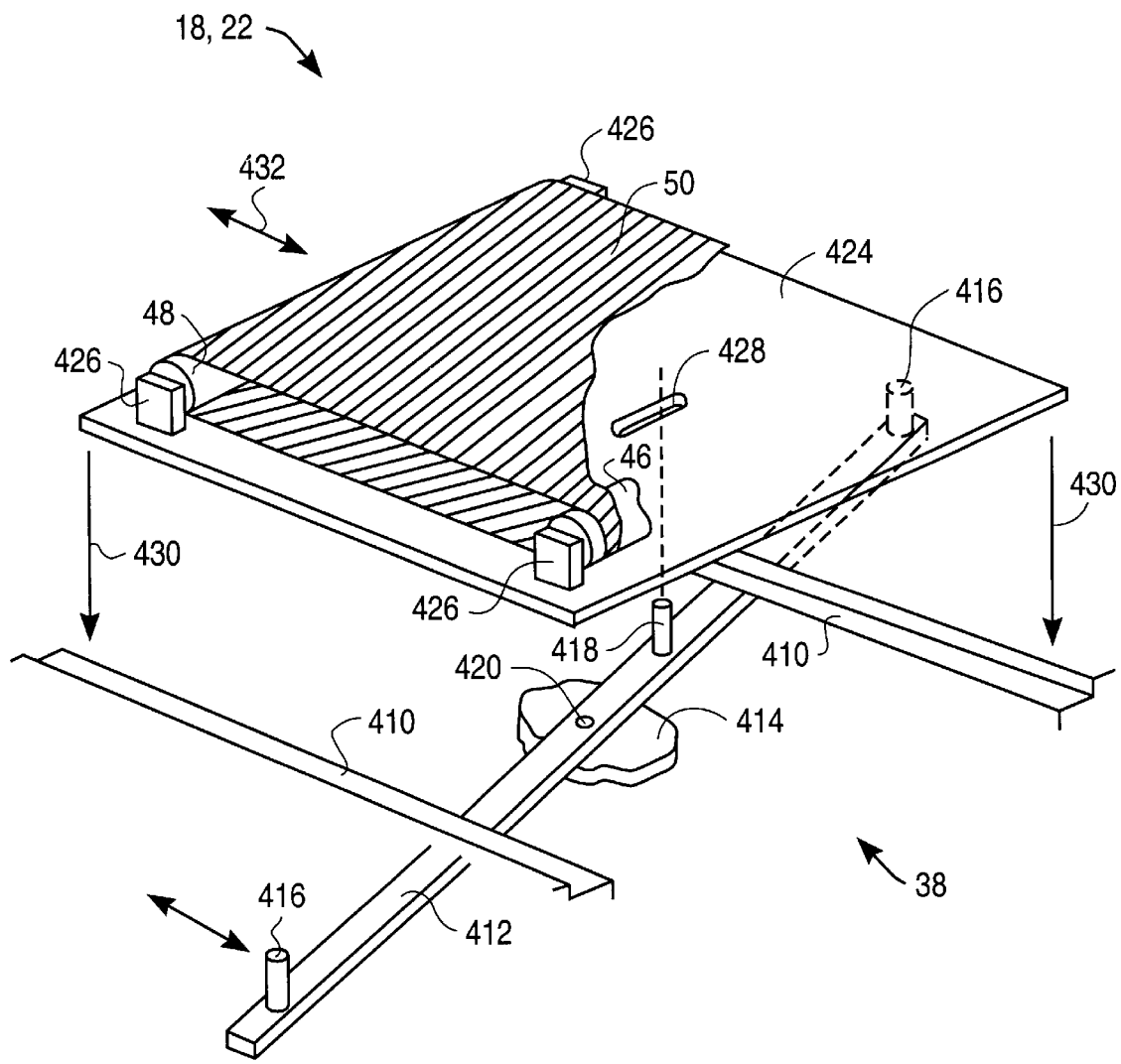
FIG. 15 is a perspective view of a portion of the inspection apparatus, illustrating how a conveyor system of the inspection apparatus is mounted to a base frame of the inspection apparatus.

FIG. 15 illustrates one of the conveyor apparatus 18 or 22 and its interaction with the base frame 38. (Compare FIG. 15 with FIG. 2).

Rails 410 are located on opposing sides of the base frame 38. A lever 412 is pivotally mounted to a portion 414 of the base frame 38. Handles 416 are mounted to ends of the lever 412. A pin 418 is secured to the lever 412 intermediate a pivot axis 420 of the lever 412 and one of the handles 416.

The conveyor apparatus 18 or 22, in addition to the front conveyor roller 46, the rear conveyor roller 48, and the conveyor belt 50 (compare with FIG. 2), further includes a conveyor slider plate 424 and a number of bracket assemblies 426. The bracket assemblies 426 are mounted directly to the conveyor slider plate 424 and the front and rear conveyor rollers 46 and 48 are, in turn, rotatably mounted between respective sets of the bracket assemblies 426.

The conveyor apparatus 18 or 22 as shown in FIG. 15 may be preassembled by a subcontractor. The subcontractor may also tension the conveyor belt 50 of the conveyor apparatus 18 or 22 before the conveyor apparatus 18 or 22 is supplied to another entity which mounts the conveyor apparatus 18 or 22 to the base frame 38.

A slot 428 is formed through the conveyor slider plate 424. The slot 428 extends in a direction transverse to the direction of motion of the conveyor belt 50, and therefore substantially parallel to the front and rear conveyor rollers 46 and 48.

The arrows 430 indicate mounting of the conveyor apparatus 18 or 22 onto the base frame 38. The conveyor slider plate 424 nestles between and on the rails 410 so as to be movable only in a direction 432 in which the rails 410 extend. The pin 418 is aligned with the slot 428 so that the pin 418 extends through the slot 428 when the conveyor slider plate 424 is located on the rails 410.

An operator may move one of the handles 416 so that the lever 412 rotates about the pivot axis 420. Rotation of lever 412 causes rotation of the pin 418 about the pivot axis 420. The pin 418 engages within the slot 428 within the conveyor slider plate 424 so that the conveyor apparatus 18 or 22 is moved backward or forward along the rails 410. The pin 418 also slides along the slot 428 when the lever 412 is rotated. Movement of the pin 418 along the slot 428 is limited by the length and positioning of the slot 428 so that movement of the conveyor apparatus 18 or 22 along the rails 410 is also limited.

Although only one of the conveyor apparatus 18 or 22 is shown in FIG. 15, it should be understood that both of the conveyor apparatus 18 and 22, as shown in FIG. 2, have a design similar to that shown in FIG. 15. The conveyor apparatus 20 is rigidly mounted to the base frame 38, so that only the conveyor apparatus 18 and 22 are able to be moved by moving its respective lever 412.

In use, the conveyor apparatus 18, 20 and 22 are mounted to the rails 410 in such a manner that adjacent front and rear rollers 46 and 48 thereof are located fairly close to one another. By so locating the conveyor apparatus 18, 20 and 22 relative to one another, smooth transition of containers from one conveyor apparatus to another is ensured. It may, however, happen from time to time that parts of containers, such as belts on luggage, become jammed between adjacent ones of the front and rear conveyor rollers 46 and 48 of two of the conveyor apparatus which are located sequentially one after the other. One of the conveyor apparatus 18 or 22 may then be moved away from the conveyor apparatus 20 by moving the handle 416 thereof, so as to part adjacent ones of the front and rear conveyor rollers 46 and 48 of the two conveyor apparatus. The jammed parts of containers can then be released from between the adjacent conveyor apparatus.

Ideally, the conveyor apparatus 18 or 22 should not, under normal operating conditions, be able to float freely on the rails 410. An additional mechanism may be provided which may lock the lever 412 releasably into a number of predetermined positions. Other mechanisms may also be provided for controlling movement of the conveyor slider plate 424 along the rails 410, and for controlling the orientation of the conveyor slider plate 424 relative to the rails 410. Such mechanisms are known in the art.

Air Conditioning

Figure 16:
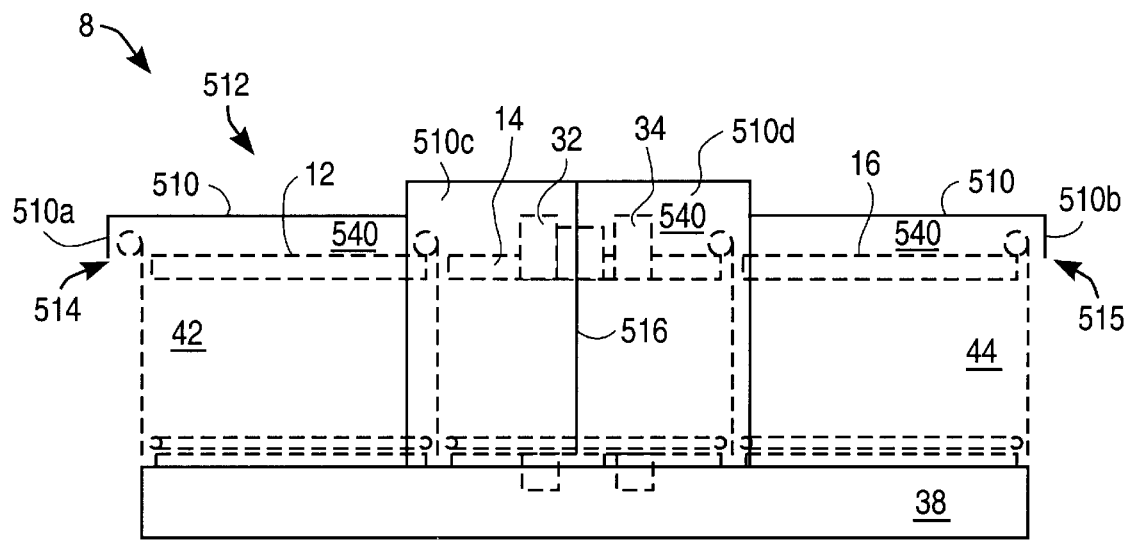
FIG. 16 is a side view of the inspection apparatus, further illustrating paneling which partially form a housing of the inspection apparatus.

FIG. 16 of the accompanying drawings illustrates the inspection apparatus 8 which further includes paneling around all the components heretofore described with the exclusion notably of the controller (see reference numeral 36 in FIG. 2) and the base frame 36. The paneling, in particular, is located around the tunneling which is formed by the loading tunnel section 12, the inspection tunnel section 14, and the unloading tunnel section 16, and around the x-ray line scanner subsystem 32 and the CT scanner subsystem 34.

The paneling includes a plurality of contiguous panels 510 which match up with one another and which, together with the base frame 38, define a housing 512 around the other components of the inspection apparatus 8.

One of the panels 510A is located at the first end 42 of the loading tunnel section 12. The panel 510A has an entry aperture 514 which is in close proximity to the first end 42 of the loading tunnel section 12. Another one of the panels 510B is located at the second end 44 of the unloading tunnel section 16. The panel 510B has an exit aperture 515 which is in close proximity to the second end of the unloading tunnel section 16.

More of the panels 510C and 510D are sliding doors which are slidably mounted to the base frame 38 to provide access to the x-ray line scanner subsystem 32 and the CT scanner subsystem 34. When the panels 510C and 510D are closed, a fairly tight interface 516 is formed between the panels 510C and 510D.

From the aforegoing can generally be noted that a housing 512 is relatively airtight.

Figure 17:
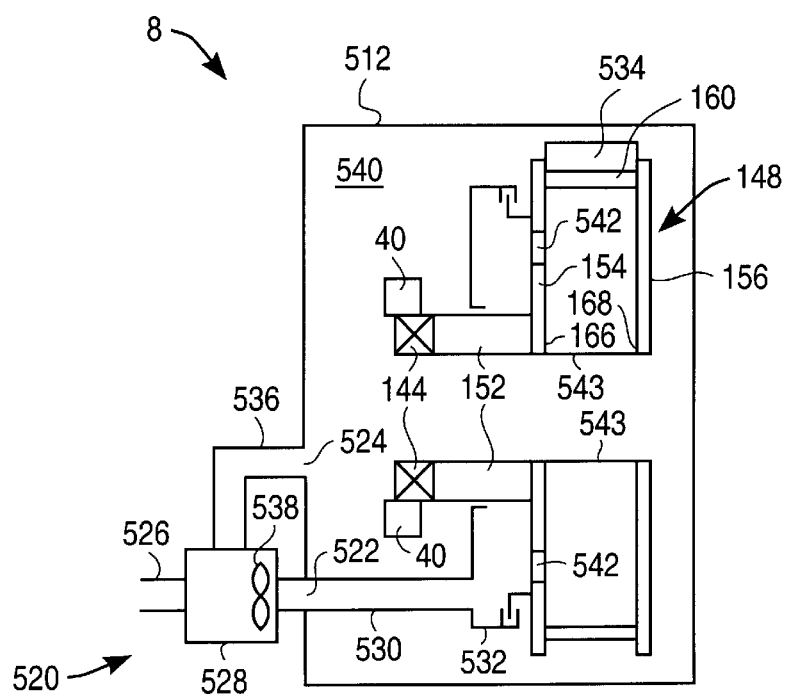
FIG. 17 is a side view of the inspection apparatus illustrating diagrammatically how the inspection apparatus is air-conditioned.

FIG. 17 is a view of the inspection apparatus 8 which further illustrates an air-conditioning apparatus 520 forming part of the inspection apparatus 8. The housing 512 is shown to have an air inlet opening 522 and an air outlet opening 524. The gantry enclosure 148 is also shown together with the ring 152 and the bearing 144 which mount the gantry enclosure 148 rotatably to the arch 40.

The air-conditioning apparatus 520 includes an air inlet duct 526, an air-conditioning unit 528, an air supply duct 530, a plenum 532, a radiator 534, and an air return duct 536.

The air-conditioning unit 528 is located externally of the housing 512 and includes a fan 538.

The plenum 532 is nonrotatably mounted to the support frame of the inspection apparatus (see reference numeral 10 in FIG. 2) and is in the form of a ring which is located around the ring 152. The plenum 532 a located externally of the gantry enclosure 148 next to the first gantry plate 154 of the gantry enclosure 148. The plenum 532 has a recessed shape which is open towards the gantry enclosure 148. A number of air passages 542 are formed through the first gantry plate 154. The (non-rotating) plenum 532 is located over the air passages 542 so that the confines of the plenum 532 are in communication with the confines of the (rotating) gantry enclosure 148.

The radiator 534 is mounted on an outer surface of the gantry enclosure 148 and holes (not shown) are formed in the gantry enclosure 148 which place the confines of the gantry enclosure 148 in communication with the radiator 534. Note that no fan is mounted within the gantry enclosure 148.

The air inlet duct 526 has one end at atmospheric pressure and another end connected to, and in communication with, the air-conditioning unit 528. The air supply duct 530 extends through the air inlet opening 522 and has one end connected to, and in communication with, the air-conditioning unit 528 and an opposing end connected to, and in communication with, the confines of the plenum 532. The air return duct 536 has one end connected to, and in communication with, the air outlet opening 524 and an opposing end connected to, and in communication with, the air-conditioning unit 528.

In use, air flows into the air-conditioning unit 528 when the fan 538 rotates. The air enters the air-conditioning unit 528 substantially at atmospheric pressure and atmospheric temperature. The air then passes through the air-conditioning unit 528. The air-conditioning unit 528 lowers the temperature of the air to substantially below atmospheric temperature. The fan 538 also increases the pressure of the air to above atmospheric pressure.

The air is then drawn into the housing 512 through the air supply duct at above atmospheric pressure and below atmospheric temperature. The air then flows through the air supply duct 530 into the plenum 532 from where the air flows through the air passages 542 into the gantry enclosure 148. A window 543 is located between the gantry apertures 166 and 168 so that a confined volume is defined by the window 546, the gantry plates 154 and 156, and the spacer 160. A number of plates (not shown) are located at selected angles around a revolution of the gantry enclosure 148 and extend radially outward so that individual confined volume pockets are defined around a revolution of the gantry enclosure. The air enters selected ones of these pockets through selected ones of the air passages 542, notably a pocket at the radiator 534 and a pocket in which the detectors (190 in FIG. 6) are located.

Air then flows from each pocket through holes (not shown) out of the gantry enclosure 148. The air flows from one pocket through some of the holes in the spacer 160 to the radiator 534. The air then passes through the radiator 534. The radiator 534 is used for cooling the x-ray tube (see reference numeral 150 in FIG. 6) and, when operated, is at a temperature substantially above atmospheric temperature. The air is used to cool the radiator 534. When the air flows through the radiator 534, the temperature of the air increases somewhat, but still remains below atmospheric temperature. The air also remains above atmospheric pressure.

Referring now to FIG. 16 and FIG. 17 in combination, once the air passes through the radiator 534, the air is located within a volume 540 which is externally of the tunneling provided by the loading, inspection and unloading tunnel sections 12, 14 and 16, respectively, and externally of the x-ray line scanner subsystem 32, and externally of the gantry enclosure 148, but still contained within the housing 512. As mentioned, the housing 512 is in close proximity to and therefore seals relatively tightly on the loading and unloading tunnel sections 12 and 16, at least to an extent sufficient to maintain the above atmospheric pressure of the air within the housing 512. As also mentioned, the interface 516 is also relatively airtight. The housing 512, in all other respects, is formed to maintain the above atmospheric pressure within the housing 512.

The air then flows from the housing 512 through the air outlet opening 524 and the air return duct 536 back to the air-conditioning unit 528. The air-conditioning unit 528 may control the ratios of air flowing respectively from the air inlet duct 526 and the air return duct 536 so that the air within the volume 540 remains above atmospheric pressure.

Because the air within the volume 540 remains above atmospheric pressure, and therefore above the pressure of the air externally of the housing 512, the air may leak slightly from between adjacent panels 510 of the housing 512 in a direction from within the housing 512 to an area around the housing 512. Because of the direction of leaking of air, ingress of dirt, moisture, and other contaminants into the housing 512 may be avoided. The positive pressure within the housing 512 thus protects the components within the housing 512 from dirt, moisture, and other contaminants.

It should be evident from the aforegoing description that the temperature of the air in the volume 540 is still below atmospheric temperature, as required for improved, more stable, and more reliable operation of components such as detector arrays which are used within the inspection apparatus 8.

What should also be noted from FIG. 17 is the positioning of the fan 538. The fan 538 is located externally of the gantry enclosure 148. The fan 538 is thus protected from gyroscopic forces which may otherwise act on the fan 538 should the fan 538 be located on the gantry enclosure 148. By so locating the fan 538, the gantry enclosure 148 can be rotated at higher speeds that would otherwise be possible. The gantry enclosure 148 can also be made larger without being limited by possible malfunctioning of the fan 538.

As previously mentioned, the invention is described by way of example only. In the aforegoing description and example is given of apparatus and a method for inspecting closed containers before being loaded into a loading bay of an airplane. Such use may, for example, be for the detection of explosives within closed containers. It should however be understood that the invention is not to be limited to the inspection of a closed containers before being loaded into a loading bay of an airplane. Various aspects of the invention may for example find application in the detection of contraband and illicit materials generally, applications beyond those linked to aviation, such as rail travel, the inspection of mail or parcels, materials testing and characterization, and the inspection of patients, in particular those applications utilizing CT technology.

What is claimed:

1. An x-ray technique-based noninstrusive inspection apparatus (8) which includes:
    first and second tunnel sections (12, 14), each having a respective first end (42) and a respective second end (44) opposing the first end thereof, the second tunnel section being located in line after the first tunnel section so that the second end of the first tunnel section is adjacent the first end of the second tunnel section;
    first and second conveyor systems (18, 20), the first conveyor system having at least one belt (50), at least partially located within the first tunnel section, which upon, movement, is capable of moving an object (60) from the first end of the first tunnel section to the second end of the first tunnel section, and the second conveyor system having at least one belt (50), at least partially located within the second tunnel section, which, upon movement, is capable of moving an object from the first end of the second tunnel section to the second end of the second tunnel section;
    an x-ray source (34) which, when operated, creates radiation within the second tunnel section;
    first and second actuation devices (242); and
    first and second radiation resistant closure members (56), the first closure member being movable by the first actuation device between an open position wherein the first end of the first tunnel section is open, and a closed position wherein the first closure member closes the first end of the first tunnel section, and the second closure member being movable by the second actuation device between an open position wherein the second end of the first tunnel section is in communication with the first end of the second tunnel section to allow for movement of an object from the first tunnel section to the second tunnel section, and a closed position wherein the second closure member substantially closes off communication between the first and second tunnel sections.

2. An x-ray technique-based nonintrusive inspection apparatus according to claim 1 which includes:
    a third tunnel section (16) having a first end (42) and a second end (44) opposing the first end thereof, the third tunnel section being located in line after the second tunnel section so that the second end of the second tunnel section is located adjacent the first end of the third tunnel section;
    a third conveyor system (22) having at least one belt (50), at least partially located within the third tunnel section, which, upon movement, is capable of moving an object from the first end of the third tunnel section to the second end of the third tunnel section;
    third and fourth actuation devices (242);
    third and fourth radiation resistant closure members (56), the third closure member being movable by the third actuation device between an open position wherein the second end of the second tunnel section is in communication with the first end of the third tunnel section to allow for movement of an object from the second tunnel section to the third tunnel section, and a closed position wherein the third closure member substantially closes off communication between the first and second tunnel sections, and the fourth closure member being movable by the fourth actuation device between an open position wherein the second end of the third tunnel section is open, and a closed position wherein the fourth closure member closes the second end of the third tunnel section.

3. An x-ray technique-based nonintrusive inspection apparatus according to claim 2 which includes first, second, third and fourth curtain rollers (54), each being rotatable by a respective one of the actuation devices, wherein the closure members are curtains and each curtain is secured to a respective curtain roller so as to be rolled onto and from the curtain roller upon rotation of the curtain roller.

4. An x-ray technique-based nonintrusive inspection apparatus according to claim 1 which includes a controller (36) which controls power supplied to the respective actuation devices.

5. An x-ray technique-based nonintrusive inspection apparatus according to claim 4 wherein the controller is programmed to synchronize the actuation devices so that, at least when the x-ray source creates radiation within the second tunnel section, at least one of the first and second closure members is in its respective closed position and at least one of the third and fourth closure members is in its respective closed position.

6. An x-ray technique-based nonintrusive inspection apparatus according to claim 5 wherein the controller turns the radiation source off when at least one of the first and second closure members is not in its respective closed position and at least one of the third and fourth closure members is not in its respective closed position.

7. A method of non-intrusively inspecting an object (60), utilizing an x-ray technique-based nonintrusive inspection apparatus, including:
    moving a first radiation resistant closure member (56A), without the object contacting the first radiation resistant closure member, into an open position wherein a first end (42) of a first tunnel section (12) is open, while a second radiation resistant closure member (56B) is in a closed position wherein it closes a second end (44) of the first tunnel section opposing the first end of the first tunnel section;
    moving the object, without the object contacting the first radiation resistant closure member, through the first end of the first tunnel section into the first tunnel section while the second closure member remains in its closed position;

moving the first closure member into a closed position wherein the first closure member closes the first end of the first tunnel section;

after movement of the first closure member into its closed position, moving the second closure member, without the object contacting the second radiation resistant closure member, into an open position wherein the second end of the first tunnel section in communication with a first end (42) of a second tunnel section (14);

moving the object, without the object contacting the second radiation resistant closure member, from the first tunnel section into the second tunnel section;

after movement of the object into the second tunnel section, moving the second closure member into its closed position as to substantially close off communication between the first and second tunnel sections; and radiating the object within the second tunnel section.

8. A method according to claim 7 wherein the confines of the second tunnel section are radiated while the object is moved into the first tunnel section.

9. A method according to claim 7 wherein the first closure member remains in its closed position while the object is moved into the second tunnel section.

10. A method according to any one of claims 7 to 9 wherein the confines of the second tunnel section are radiated while the object is moved into the second tunnel section.

11. An x-ray technique-based nonintrusive inspection apparatus (8) which includes:

at least a first tunnel section (12) having first and second opposed ends (42, 44);

a conveyor system (18,20) operable to move an object (60) through the first end into the first tunnel section;

an x-ray source (34) which, when operated, creates radiation within the first tunnel section;

at least a first actuation device (242); and at least a first radiation resistant closure member (56) which is movable by the actuation device between an open position wherein the first end of the first tunnel is open to allow for the object to be moved by the conveyor system through the first opening into the first tunnel section without the object contacting the first radiation resistant closure member, and a closed position wherein the first closure member closes the first end of the first tunnel section.

12. An x-ray technique-based nonintrusive inspection apparatus according to claim 11 which includes:

a support frame; and at least a first curtain roller (54) which is rotatably mounted to the support frame, the first curtain roller being rotatable by the actuation device, wherein the first closure member is a radiation resistant curtain which is secured to the curtain roller so as to be rolled onto and from the curtain roller upon rotation of the curtain roller.

13. An x-ray technique-based nonintrusive inspection apparatus according to claim 12, which includes a tensioning roller (244) rotatably mounted to the support frame and connected to the curtain, the tensioning roller tending to roll the curtain from the curtain roller.

14. An x-ray technique-based nonintrusive inspection apparatus according to claim 13 which includes a spring (248) which is biased between the frame and the tensioning roller so as to tend to rotate the tensioning roller.

15. An x-ray technique-based nonintrusive inspection apparatus according to claim 13 which includes a sheet (246) which has a first portion attached to the curtain roller and rolls with the curtain onto and from the curtain roller, and a second portion attached to the tensioning roller, so as to connect the tensioning roller with the curtain.

16. An x-ray technique-based nonintrusive inspection apparatus according to claim 13 wherein the curtain hangs from one side of the curtain roller and the tensioning roller is located on the same side of the curtain roller as the side of the curtain roller from which the curtain hangs.

* * * * *